(12) United States Patent
Holmes et al.

(10) Patent No.: US 8,669,047 B2
(45) Date of Patent: *Mar. 11, 2014

(54) REAL-TIME DETECTION OF INFLUENZA VIRUS

(75) Inventors: Elizabeth A. Holmes, Palo Alto, CA (US); Ian Gibbons, Portola Valley, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/187,960

(22) Filed: Jul. 21, 2011

(65) Prior Publication Data

US 2012/0034598 A1 Feb. 9, 2012

Related U.S. Application Data

(63) Continuation of application No. 11/746,535, filed on May 9, 2007, now Pat. No. 8,007,999.

(60) Provisional application No. 60/799,442, filed on May 10, 2006, provisional application No. 60/800,939, filed on May 16, 2006.

(51) Int. Cl.
| | | |
|---|---|---|
| *C12Q 1/70* | (2006.01) | |
| *G01N 33/536* | (2006.01) | |
| *G01N 33/53* | (2006.01) | |
| *C12N 7/02* | (2006.01) | |
| *C12N 5/07* | (2010.01) | |
| *A01N 63/00* | (2006.01) | |
| *A61K 39/395* | (2006.01) | |
| *A61K 39/42* | (2006.01) | |
| *A61K 39/145* | (2006.01) | |
| *A61K 35/12* | (2006.01) | |

(52) U.S. Cl.
USPC ............... 435/5; 436/536; 435/7.1; 435/239; 435/339; 424/141.1; 424/147.1; 424/159.1; 424/206.1; 424/209.1; 424/93.6; 424/520

(58) Field of Classification Search
None
See application file for complete search history.

(56) References Cited

U.S. PATENT DOCUMENTS

| | | |
|---|---|---|
| 4,003,379 A | 1/1977 | Ellinwood |
| 4,146,029 A | 3/1979 | Ellinwood |
| 4,347,176 A | 8/1982 | Mehta |
| 4,731,726 A | 3/1988 | Allen |
| 4,793,825 A | 12/1988 | Benjamin et al. |
| 4,910,131 A | 3/1990 | Mellman et al. |
| 4,920,213 A | 4/1990 | Dale et al. |
| 4,946,795 A | 8/1990 | Gibbons et al. |
| 5,089,229 A | 2/1992 | Heidt et al. |
| 5,104,813 A | 4/1992 | Besemer et al. |
| 5,162,237 A | 11/1992 | Messenger et al. |
| 5,279,607 A | 1/1994 | Schentag et al. |
| 5,281,395 A | 1/1994 | Markart et al. |
| 5,380,487 A | 1/1995 | Choperena et al. |
| 5,443,790 A | 8/1995 | Coeurveille et al. |
| 5,472,603 A | 12/1995 | Schembri |
| 5,554,539 A | 9/1996 | Chadney et al. |
| 5,578,269 A | 11/1996 | Yaremko et al. |
| 5,624,850 A | 4/1997 | Kumar et al. |
| 5,670,375 A | 9/1997 | Seaton et al. |
| 5,674,698 A | 10/1997 | Zarling et al. |
| 5,716,852 A | 2/1998 | Yager et al. |
| 5,744,366 A | 4/1998 | Kricka et al. |
| 5,797,898 A | 8/1998 | Santini et al. |
| 5,801,057 A | 9/1998 | Smart et al. |
| 5,807,375 A | 9/1998 | Gross et al. |
| 5,820,548 A | 10/1998 | Sieben et al. |
| 5,832,296 A | 11/1998 | Wang et al. |
| 5,842,787 A | 12/1998 | Kopf-Sill et al. |
| 5,848,991 A | 12/1998 | Gross et al. |
| 5,874,214 A | 2/1999 | Nova et al. |
| 5,885,470 A | 3/1999 | Parce et al. |
| 5,902,549 A | 5/1999 | Mimura et al. |
| 5,942,443 A | 8/1999 | Parce et al. |
| 5,961,451 A | 10/1999 | Reber et al. |
| 5,961,923 A | 10/1999 | Nova et al. |
| 5,976,896 A | 11/1999 | Kumar et al. |
| 5,980,830 A | 11/1999 | Savage et al. |
| 6,046,056 A | 4/2000 | Parce et al. |
| 6,074,616 A | 6/2000 | Buechler et al. |
| 6,123,861 A | 9/2000 | Santini et al. |
| 6,156,181 A | 12/2000 | Parce et al. |
| 6,174,675 B1 | 1/2001 | Chow et al. |
| 6,176,962 B1 | 1/2001 | Soane et al. |
| 6,200,814 B1 | 3/2001 | Malmqvist et al. |
| 6,204,068 B1 | 3/2001 | Soini et al. |

(Continued)

FOREIGN PATENT DOCUMENTS

| | | |
|---|---|---|
| CN | 2559986 | 7/2003 |
| EP | 1498067 A1 | 1/2005 |

(Continued)

OTHER PUBLICATIONS

U.S. Appl. No. 12/221,816, filed Aug. 6, 2008, Roy et al.

(Continued)

*Primary Examiner* — Benjamin P Blumel

(57) ABSTRACT

The present invention provides system and methods for detecting an analyte indicative of an influenza viral infection in a sample of bodily fluid. The present invention also provides for systems and method for detection a plurality of analytes, at least two of which are indicative of an influenza viral infection in a sample of bodily fluid.

12 Claims, 13 Drawing Sheets

(56) References Cited

U.S. PATENT DOCUMENTS

| | | |
|---|---|---|
| 6,221,677 B1 | 4/2001 | Wu et al. |
| 6,245,057 B1 | 6/2001 | Sieben et al. |
| 6,299,839 B1 | 10/2001 | Karunaratne et al. |
| 6,319,668 B1 | 11/2001 | Nova et al. |
| 6,340,588 B1 | 1/2002 | Nova et al. |
| 6,352,854 B1 | 3/2002 | Nova et al. |
| 6,368,275 B1 | 4/2002 | Sliwa et al. |
| 6,372,428 B1 | 4/2002 | Nova et al. |
| 6,375,469 B1 | 4/2002 | Brown |
| 6,429,025 B1 | 8/2002 | Parce et al. |
| 6,440,725 B1 | 8/2002 | Pourahmadi et al. |
| 6,464,687 B1 | 10/2002 | Ishikawa et al. |
| 6,482,593 B2 | 11/2002 | Walt |
| 6,491,666 B1 | 12/2002 | Santini, Jr. et al. |
| 6,503,231 B1 | 1/2003 | Prausnitz et al. |
| 6,527,762 B1 | 3/2003 | Santini et al. |
| 6,542,717 B1 | 4/2003 | Zimmerman et al. |
| 6,544,732 B1 | 4/2003 | Chee et al. |
| 6,551,838 B2 | 4/2003 | Santini et al. |
| 6,591,124 B2 | 7/2003 | Sherman et al. |
| 6,632,216 B2 | 10/2003 | Houzego et al. |
| 6,649,358 B1 | 11/2003 | Parce et al. |
| 6,663,003 B2 | 12/2003 | Johnson et al. |
| 6,789,510 B1 | 9/2004 | Lee |
| 6,832,296 B2 | 12/2004 | Hooker |
| 6,849,237 B2 | 2/2005 | Housefield et al. |
| 6,878,755 B2 | 4/2005 | Singh et al. |
| 6,887,202 B2 | 5/2005 | Currie et al. |
| 6,923,764 B2 | 8/2005 | Aceti et al. |
| 6,927,851 B2 | 8/2005 | McCaffrey et al. |
| 6,929,636 B1 | 8/2005 | Von Alten |
| 6,949,377 B2 | 9/2005 | Ho |
| 6,966,880 B2 | 11/2005 | Boecker et al. |
| 7,039,453 B2 | 5/2006 | Mullick et al. |
| 7,052,831 B2 | 5/2006 | Fletcher et al. |
| 7,105,183 B2 | 9/2006 | McGrath |
| 7,112,444 B2 | 9/2006 | Beebe et al. |
| 7,178,386 B1 | 2/2007 | Gamble et al. |
| 7,201,872 B2 | 4/2007 | Meron |
| 7,291,497 B2 | 11/2007 | Holmes et al. |
| 7,459,305 B2 | 12/2008 | Levy |
| 7,635,594 B2 | 12/2009 | Holmes et al. |
| 7,636,667 B2 | 12/2009 | Brown |
| 7,807,197 B2 | 10/2010 | Lee et al. |
| 8,007,999 B2 * | 8/2011 | Holmes et al. ............ 435/5 |
| 8,055,329 B2 | 11/2011 | Kimchy et al. |
| 2001/0019831 A1 | 9/2001 | Phillips et al. |
| 2001/0051340 A1 | 12/2001 | Singh et al. |
| 2001/0051766 A1 | 12/2001 | Gazdzinski |
| 2001/0053535 A1 | 12/2001 | Bashir et al. |
| 2002/0001854 A1 | 1/2002 | Lee |
| 2002/0034757 A1 | 3/2002 | Cubicciotti |
| 2002/0055094 A1 | 5/2002 | Reece et al. |
| 2002/0055127 A1 | 5/2002 | Gindilis |
| 2002/0072733 A1 | 6/2002 | Flaherty |
| 2002/0092770 A1 | 7/2002 | Hedberg et al. |
| 2002/0110496 A1 | 8/2002 | Samsoondar |
| 2002/0114739 A1 | 8/2002 | Weigl et al. |
| 2002/0120187 A1 | 8/2002 | Eiffert et al. |
| 2002/0132226 A1 | 9/2002 | Nair et al. |
| 2002/0143437 A1 | 10/2002 | Handique et al. |
| 2003/0014362 A1 | 1/2003 | Yim |
| 2003/0049833 A1 | 3/2003 | Chen et al. |
| 2003/0049865 A1 | 3/2003 | Santini, Jr. et al. |
| 2003/0061687 A1 | 4/2003 | Hansen et al. |
| 2003/0069560 A1 | 4/2003 | Adamis et al. |
| 2003/0097092 A1 | 5/2003 | Flaherty |
| 2003/0104590 A1 | 6/2003 | Santini et al. |
| 2003/0117491 A1 | 6/2003 | Avni et al. |
| 2003/0143551 A1 | 7/2003 | Cattell |
| 2003/0148362 A1 | 8/2003 | Luka |
| 2003/0153900 A1 | 8/2003 | Aceti et al. |
| 2003/0167000 A1 | 9/2003 | Mullick et al. |
| 2003/0185706 A1 | 10/2003 | Ribi |
| 2003/0191430 A1 | 10/2003 | D'Andrea et al. |
| 2003/0208113 A1 | 11/2003 | Mault et al. |
| 2003/0208133 A1 | 11/2003 | Mault |
| 2003/0210607 A1 | 11/2003 | Gilbert et al. |
| 2003/0211007 A1 | 11/2003 | Maus et al. |
| 2003/0211618 A1 | 11/2003 | Patel |
| 2003/0214057 A1 | 11/2003 | Huang |
| 2004/0005247 A1 | 1/2004 | Karp |
| 2004/0005582 A1 | 1/2004 | Shipwash |
| 2004/0014202 A1 | 1/2004 | King et al. |
| 2004/0033553 A1 | 2/2004 | Littarru et al. |
| 2004/0053290 A1 | 3/2004 | Terbrueggen et al. |
| 2004/0086872 A1 | 5/2004 | Childers et al. |
| 2004/0096959 A1 | 5/2004 | Stiene et al. |
| 2004/0109793 A1 | 6/2004 | McNeely et al. |
| 2004/0121305 A1 | 6/2004 | Wiegand et al. |
| 2004/0122486 A1 | 6/2004 | Stahmann et al. |
| 2004/0213825 A1 | 10/2004 | Levy |
| 2004/0228766 A1 | 11/2004 | Witty et al. |
| 2004/0260204 A1 | 12/2004 | Boecker et al. |
| 2005/0009101 A1 | 1/2005 | Blackburn |
| 2005/0019836 A1 | 1/2005 | Vogel et al. |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1 | 5/2005 | Holmes |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | McDevitt et al. |
| 2005/0137481 A1 | 6/2005 | Sheard et al. |
| 2005/0147559 A1 | 7/2005 | Von Alten |
| 2005/0209565 A1 | 9/2005 | Yuzhakov et al. |
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2006/0019319 A1 | 1/2006 | Billadeau et al. |
| 2006/0029924 A1 | 2/2006 | Brewster et al. |
| 2006/0062852 A1 | 3/2006 | Holmes |
| 2006/0078998 A1 | 4/2006 | Puskas et al. |
| 2006/0106316 A1 | 5/2006 | Palti |
| 2006/0177873 A1 | 8/2006 | Dowd et al. |
| 2006/0182738 A1 | 8/2006 | Holmes |
| 2006/0211933 A1 | 9/2006 | Zimmermann et al. |
| 2006/0257941 A1 | 11/2006 | McDevitt et al. |
| 2006/0264779 A1 | 11/2006 | Kemp et al. |
| 2006/0264780 A1 | 11/2006 | Holmes et al. |
| 2006/0264781 A1 | 11/2006 | Gibbons et al. |
| 2006/0264782 A1 | 11/2006 | Holmes et al. |
| 2006/0264783 A1 | 11/2006 | Holmes et al. |
| 2007/0059196 A1 | 3/2007 | Brister et al. |
| 2007/0166195 A1 | 7/2007 | Padmanabhan et al. |
| 2007/0224084 A1 | 9/2007 | Holmes et al. |
| 2007/0264629 A1 | 11/2007 | Holmes et al. |
| 2008/0009766 A1 | 1/2008 | Holmes et al. |
| 2008/0113391 A1 | 5/2008 | Gibbons et al. |
| 2010/0074799 A1 | 3/2010 | Kemp et al. |
| 2010/0081144 A1 | 4/2010 | Holmes et al. |
| 2010/0248277 A1 | 9/2010 | Gibbons et al. |
| 2011/0003699 A1 | 1/2011 | Yoder et al. |
| 2011/0104826 A1 | 5/2011 | Gibbons et al. |
| 2011/0166553 A1 | 7/2011 | Holmes et al. |

FOREIGN PATENT DOCUMENTS

| | | |
|---|---|---|
| JP | H 07-304799 | 11/1995 |
| JP | 2002-538440 | 8/2000 |
| JP | 2002-511965 | 4/2002 |
| JP | 2004-527825 | 8/2002 |
| JP | 2005-130855 | 5/2005 |
| JP | 2007-187677 | 7/2007 |
| WO | WO 94/01165 A1 | 1/1994 |
| WO | WO 01/35928 A1 | 5/2001 |
| WO | WO 01/64344 A2 | 9/2001 |
| WO | WO 01/64344 A3 | 3/2002 |
| WO | WO 03/066128 A2 | 8/2003 |
| WO | WO 03/066128 A3 | 12/2003 |
| WO | WO 2005/024437 A1 | 3/2005 |

(56) References Cited

FOREIGN PATENT DOCUMENTS

| WO | WO 2005/031355 A1 | 4/2005 |
| --- | --- | --- |
| WO | WO 2005/065157 A2 | 7/2005 |
| WO | WO 2005/065538 A2 | 7/2005 |
| WO | WO 2005/065157 A3 | 10/2005 |
| WO | WO 2005/121367 A1 | 12/2005 |
| WO | WO 2007/120904 A2 | 10/2007 |
| WO | WO 2007/120904 A3 | 12/2008 |

OTHER PUBLICATIONS

Bawendi, et al. The quantum-mechanics of larger semiconductor clusters. Annu. Rev. Phys. Chem. 1990; 41:477-496.

BD Biosciences, Directigen FluA&B Assay Manual. Oct. 11, 2006, pp. 1-11.

Beier, et al. Versatile derivatisation of solid support media for covalent bonding on DNA-microchips. Nucleic Acids Res. 1999; 27:1970-1977.

Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.

Bhatia, et al. Use of thiol-terminal silanes and heterobifunctional crosslinkers for immobilization of antibodies on silica surfaces. Anal Biochem. 1989; 178(2):408-13.

Bruchez, et al. Semiconductor nanocrystals as fluorescent biological labels. Science. 1998; 281(5385):2013-6.

Celebre, et al. A comparative study of efficiencies of fibre optic and prism TIRF sensors. Meas. Sci. Technol. 1992; 3:1166-1173.

Chan. Quantum dot bioconjugates for ultrasensitive nonisotopic detection. Science. 1998; 281(5385):2016-8.

Chang, et al. Micromachining & Microfabrication. SPIE Optical Engineering Press. Bellingham, Wash. 1997. (Cover pages and table of contents only).

Charles, et al. Synthesis of a fluorescent analog of polychlorinated biphenyls for use in a continuous flow immunosensor assay. Bioconjug Chem. 1995; 6(6):691-4.

Duffy, et al. Rapid Prototyping of Microfluidic Systems in Poly(dimethylsiloxane). Analytical Chemistry. 1998; 70(23):4974-4984.

European search report dated Jun. 2, 2009 for Application No. 07762092.

Gavin, et al. Review of Rapid Diagnostic Tests for Influenza. Clinical and Applied Immunology Reviews. 2004; 4(3):151-172.

Harlow, et al. Antibodies: A Laboratory Manual. Cold Spring Harbor Laboratory. New York. 1988. (Cover pages and table of contents only).

Harrison's Principles of Internal Medicine, Part 2 Cardinal Manifestations of Disease, Ch. 60 (12th ed. 1991; pp. 338-343.).

International search report dated Jan. 22, 2008 for PCT Application No. US2006/042563.

International search report dated Jul. 4, 2005 for PCT Application No. US2004/029462.

International search report dated Aug. 11, 2008 for PCT Application No. US2007/068665.

International search report dated Sep. 9, 2008 for PCT Application No. US2007/023904.

International search report dated Dec. 8, 2008 for PCT Application No. US2006/011090.

Jaeger. Introduction to Microelectronic fabrication. Addison-Wesley Pubishing Co. Reading Mass. 1988. (Cover pages and table of Contents only).

Kessler, et al. Use of the DNA flow-thru chip, a three-dimensional biochip, for typing and subtyping of influenza viruses. J Clin Microbiol. May 2004;42(5):2173-85.

Kilbourne, et al. Independent and disparate evolution in nature of influenza A virus hemagglutinin and neuraminidase glycoproteins. Proc Natl Acad Sci U S A. Jan. 1990;87(2):786-90.

Lee, et al. Microfluidic enzyme-linked immunosorbent assay technology. Adv Clin Chem. 2006;42:255-95.

Liu, et al. Validation of A fully integrated microfluidic array device for influenza A subtype identification and sequencing. Anal Chem. Jun. 15, 2006;78(12):4184-93.

Lupiani, et al. Improved diagnostic tests for Avian influenza surveillance, 2005. Proceedings of the Institute of Food Technologists' First Annual Forod protection and Defense Research Conference.

Mukerjee, et al. Microneedle array for transdermal biological fluid extraction and in situ analysis. Sensors and Actuators A. 2004; 114:267-275.

Pescovitz, D. Sniffing out airborne diseases. Lab Note: Research from the College of Engineering, University of California, Berkeley, 2004. Available online at http://www.coe.berkeley.edu/labnotes/0904/pisano.html. Accessed Jan. 28, 2011.

Preininger, et al. Polymer-coated optical fibres for application in a direct evanescent wave immunoassay. Analytica Chimica Acta, 2000; 403, 67-76.

Rai-Choudhury, ed., Handbook of Microlithography, Micromachining & Microfabrication. SPIE Optical Engineering Press. Bellingham, Wash. 1997. (Cover pages and table of contents only).

Runyan, et al. Semiconductor integrated circuit processing technology. Addison-Wesley Publishing Co., Reading Mass. 1990. (Cover pages and table of contents only).

Sambrook, et al. Molecular Cloning: A Laboratory Manual. Cold Spring Harbor Laboratory Press. New York. 2001. (Cover pages and table of contents only).

Sapsford, et al. Demonstration of four immunoassay formats using the array biosensor. Anal Chem. 2002; 74(5):1061-8.

Scheurle, et al. HER-2/neu expression in archival non-smaill cell lung carcinomas using FDA-approved hercep test. Anticancer Res. 2000; 20:2091-2096.

Spira, et al. The identification of monoclonal class switch variants by sib selection and an ELISA assay. J Immunol Methods. 1984;74(2):307-15.

Steplewski, et al. Isolation and characterization of anti-monosialoganglioside monoclonal antibody 19-9 class-switch variants. Proc Natl Acad Sci U S A. 1985; 82(24):8653-7.

Stevens, et al. Glycan microarray analysis of the hemagglutinins from modern and pandemic influenza viruses reveals different receptor specificities. J Mol Biol. Feb. 3, 2006;355(5):1143-55.

Tedeschi, et al. Antibody immobilisation on fibre optic TIRF sensors. Biosens Bioelectron. 2003; 19(2):85-93.

Yan, et al. Multiplexed flow cytometric immunoassay for influenza virus detection and differentiation. Anal Chem. Dec. 1, 2005;77(23):7673-8.

Geddes, et al. The impedance of stainless-steel electrodes. Med Biol Eng. Sep. 1971;9(5):511-21.

Hirsch, et al. The electrical conductivity of blood. I: Relationship to erythrocyte concentration. Blood. Nov. 1950;5(11):1017-35.

Mohapatra, et al. Blood resistivity and its implications for the calculation of cardiac output by the thoracic electrical impedance technique. Intensive Care Med. Aug. 1977;3(2):63-7.

U.S. Appl. No. 13/286,168, filed Oct. 31, 2011, Holmes et al.

Broadcaster Moira Gunn with Elizabeth Homes, recorded Mar. 5, 2005 on Biotech Nation.

Pal, et al. An integrated microfluidic device for influenza and other genetic analyses. Lab Chip. Oct. 2005;5(10):1024-32. Epub Aug. 18, 2005.

Patofsky, et al. Electrical detection of single viruses. Proc Natl Acad Sci U S A. Sep. 28, 2004;101(39):14017-22. Epub Sep. 13, 2004.

Red Herring. Stopping bad reactions. Red Herring. Dec. 26, 2005.

U.S. Appl. No. 13/629,577, filed Sep. 27, 2012, Holmes et al.

U.S. Appl. No. 13/647,325, filed Oct. 8, 2012, Holmes et al.

European search report and search opinion dated May 29, 2012 for EP Application No. 11180769.9.

U.S. Appl. No. 13/366,193, filed Feb. 3, 2012, Holmes et al.

European search report and search opinion dated Mar. 6, 2012 for EP Application No. 10179887.4.

European search report dated Feb. 7, 2012 for EP Application No. 11180769.9.

Office action dated Jan. 5, 2010 for U.S. Appl. No. 11/388,415.

Office action dated Jan. 8, 2013 for U.S. Appl. No. 11/388,415.

Office action dated Feb. 2, 2011 for U.S. Appl. No. 11/746,535.

Office action dated Feb. 22, 2008 for U.S. Appl. No. 11/746,535.

(56) References Cited

OTHER PUBLICATIONS

Office action dated Feb. 27, 2009 for U.S. Appl. No. 11/388,723.
Office action dated Mar. 5, 2009 for U.S. Appl. No. 11/388,823.
Office action dated Mar. 5, 2010 for U.S. Appl. No. 11/746,535.
Office action dated Mar. 17, 2009 for U.S. Appl. No. 11/388,415.
Office action dated Mar. 21, 2008 for U.S. Appl. No. 11/388,723.
Office action dated Mar. 21, 2011 for U.S. Appl. No. 11/388,415.
Office action dated Apr. 1, 2010 for U.S. Appl. No. 11/388,824.
Office action dated Apr. 4, 2013 for U.S. Appl. No. 12/986,954.
Office action dated Apr. 5, 2010 for U.S. Appl. No. 11/554,509.
Office action dated Apr. 8, 2009 for U.S. Appl. No. 11/389,410.
Office action dated Apr. 13, 2012 for U.S. Appl. No. 11/554,509.
Office action dated Apr. 29, 2009 for U.S. Appl. No. 11/389,409.
Office action dated Apr. 30, 2009 for U.S. Appl. No. 11/388,824.
Office action dated Apr. 30, 2013 for U.S. Appl. No. 13/647,325.
Office action dated May 22, 2009 for U.S. Appl. No. 11/746,535.
Office action dated May 29, 2012 for U.S. Appl. No. 12/986,954.
Office action dated Jun. 1, 2007 for U.S. Appl. No. 11/389,409.
Office action dated Jun. 1, 2012 for U.S. Appl. No. 11/388,823.
Office action dated Jun. 9, 2010 for U.S. Appl. No. 11/746,535.
Office action dated Jun. 11, 2012 for U.S. Appl. No. 11/388,415.
Office action dated Jul. 18, 2012 for U.S. Appl. No. 12/576,197.
Office action dated Jul. 25, 2008 for U.S. Appl. No. 11/389,409.
Office action dated Jul. 27, 2011 for U.S. Appl. No. 11/554,509.
Office action dated Jul. 29, 2011 for U.S. Appl. No. 12/986,954.
Office action dated Aug. 24, 2010 for U.S. Appl. No. 11/388,415.
Office action dated Aug. 27, 2010 for U.S. Appl. No. 11/388,823.
Office action dated Aug. 29, 2008 for U.S. Appl. No. 11/388,823.
Office action dated Aug. 31, 2011 for U.S. Appl. No. 12/221,816.
Office action dated Sep. 5, 2008 for U.S. Appl. No. 11/388,723.
Office action dated Sep. 11, 2008 for U.S. Appl. No. 11/389,409.
Office action dated Sep. 22, 2011 for U.S. Appl. No. 12/576,197.
Office action dated Oct. 6, 2008 for U.S. Appl. No. 11/746,535.
Office action dated Oct. 17, 2008 for U.S. Appl. No. 11/389,410.
Office action dated Nov. 9, 2011 for U.S. Appl. No. 11/388,823.
Office action dated Dec. 11, 2012 for U.S. Appl. No. 12/750,518.
Office action dated Dec. 22, 2009 for U.S. Appl. No. 11/388,823.
Office action dated Dec. 22, 2010 for U.S. Appl. No. 11/554,509.
Office action dated Feb. 17, 2009 for U.S. Appl. No. 11/202,231.
Office action dated Feb. 22, 2008 for U.S. Appl. No. 11/202,231.
Office action dated Mar. 3, 2011 for U.S. Appl. No. 11/202,206.
Office action dated Mar. 7, 2006 for U.S. Appl. No. 10/937,872.
Office action dated Mar. 16, 2011 for U.S. Appl. No. 11/202,231.
Office action dated Mar. 18, 2008 for U.S. Appl. No. 11/202,206.
Office action dated Mar. 22, 2010 for U.S. Appl. No. 11/202,206.
Office action dated Apr. 18, 2007 for U.S. Appl. No. 10/937,872.
Office action dated Jun. 21, 2007 for U.S. Appl. No. 11/202,231.
Office action dated Jul. 28, 2009 for U.S. Appl. No. 11/202,206.
Office action dated Sep. 1, 2005 for U.S. Appl. No. 10/937,872.
Office action dated Oct. 26, 2006 for U.S. Appl. No. 10/937,872.
Office action dated Nov. 5, 2009 for U.S. Appl. No. 11/202,231.
Office action dated Nov. 22, 2011 for U.S. Appl. No. 11/202,231.
Office action dated Dec. 19, 2008 for U.S. Appl. No. 11/202,206.
U.S. Appl. No. 13/896,171, filed May 16, 2013, Holmes et al.
International search report and written opinion dated Sep. 16, 2008 for PCT/US2007/009878.
Office action dated Jun. 5, 2013 for U.S. Appl. No. 12/750,518.
Office action dated Jun. 24, 2013 for U.S. Appl. No. 13/436,568.
Khan, et al. Detection of influenza virus neuraminidase-specific antibodies by an enzyme-linked immunosorbent assay. J Clin Microbiol. Jul. 1982;16(1):115-22.
Office action dated Sep. 4, 2013 for U.S. Appl. No. 11/388,823.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05 (in Japanese with English translation).
Ray, et al. Distinct hemagglutinin and neuraminidase epitopes involved in antigenic variation of recent human parainfluenza virus type 2 isolates. Virus Res. Jun. 1992;24(1):107-13.
U.S. Appl. No. 14/050,235, filed Oct. 9, 2013.
Office action dated Oct. 31, 2013 for U.S. Appl. No. 12/986,954.

\* cited by examiner

Plasma Effect

Two Step

Competitive Binding

REAL-TIME DETECTION OF INFLUENZA VIRUS

CROSS-REFERENCE

This application is a continuation of U.S. patent application Ser. No. 11/746,535, filed on May 9, 2007 now U.S Pat. No. 8,007,999, which claims the benefit of U.S. Provisional Patent Application No. 60/799,442, filed May 10, 2006 and U.S. Provisional Patent Application No. 60/800,939, filed May 16, 2006, each of which is incorporated herein by reference in their entirety for all purposes. This application is related to application Ser. No. 11/389,409, filed on Mar. 24, 2006, which is incorporated herein by reference in its entirety.

BACKGROUND OF THE INVENTION

Influenza ("flu") is an infectious disease capable of inflicting upon a wide variety of hosts, including birds and mammals. Flu is caused by an RNA virus of the orthomyxoviridae family (that generally comprises the type A, B, and C influenza viruses). Avian flu is caused by a virus of this family adapted to birds, thus it is also named bird flu, avian influenza, or bird influenza. A current pandemic threat stems from an unprecedented outbreak of the H5N1 strain of the influenza A virus in Asia and Europe. This strain has an ability to mutate and adapt itself to a wide range of hosts, including birds and humans. The Homeland Security Council issued the "National Strategy for Pandemic Influenza" ("The Strategy") in November of 2005 in response to the current pandemic threat. A critical part of that initiative focuses on the rapid identification of Avian Flu in patients and birds. The strategy seeks to improve the surveillance and detection of the Avian Flu.

As of November 2005, the virus causing the Avian Flu pandemic threat was known to have infected 121 people in four countries, resulting in 62 deaths over the past two years. Those infected with H5N1 had, in almost all cases, extensive physical contact with infected birds. Although the virus has not yet shown an ability to transmit efficiently between humans, as is seen with the annual human influenza virus epidemic, it raises a serious concern that it will acquire this capability through genetic mutation or exchange of genetic material with a human influenza virus.

Influenza causes approximately 36,000 deaths and more than 200,000 hospitalizations each year in the U.S. alone, and costs the U.S. over $10 billion annually. In addition, the last three pandemics, in 1918, 1957, and 1968, killed approximately 40 million, 2 million, and 1 million people worldwide, respectively.

There remains a pressing need for devices and methods that can accurately and rapidly detect the presence of Avian Flu to provide an early warning of a pandemic in order to contain the spread of the disease. An ideal system would (1) allow for retrieval, transmission, and analysis of data from such devices; and (2) provide a real-time warning system to health and government officials. The present invention satisfies this need and provides related advantages.

SUMMARY OF INVENTION

The present invention provides a system for detecting an analyte indicative of an influenza viral infection in a bodily fluid from a subject. The system typically comprises a) a fluidic device, said fluidic device comprising a sample collection unit and an assay assembly, wherein said sample collection unit allows a sample of bodily fluid suspected to contain said analyte to react with reactants contained within said assay assembly to yield a detectable signal indicative of the presence of said analyte; b) a reader assembly comprising a detection assembly for detecting said detectable signal; and c) a communication assembly for transmitting said detected signal to said external device. The system is capable of detecting an influenza type A, B, and/or C viral infection. In general, the analyte may comprise a surface glycoprotein of an influenza virus, which can be hemagglutinin (e.g., H1, H2, H3, H4, H5, H6, H7, H8, H9, H10, H11, H12, H13, H14, H15, and H16) and/or neuraminidase (e.g., N1, N2, N3, N4, and N5). The bodily fluid can be drawn from a subject selected from the group consisting of human, poultry and wild birds.

The present invention also provides a system for detecting a plurality of analytes, at least two of which are indicative of an influenza viral infection in a bodily fluid from a subject. The system typically comprises a) a fluidic device, said fluidic device comprising a sample collection unit and an assay assembly, wherein said sample collection unit allows a sample of bodily fluid suspected to contain said plurality of analytes to react with reactants contained within said assay assembly to yield one or more detectable signals indicative of the presence of said at least two analytes; b) a reader assembly comprising a detection assembly for detecting said one or more detectable signals; and c) a communication assembly for transmitting said detected signal to said external device.

The present invention further provides a method of using the subject systems. In one aspect, the present invention provides a method for detecting an analyte indicative of an influenza infection in a bodily fluid of a subject. The method involves the steps of a) providing a subject system; b) allowing a sample of bodily fluid to react with the reactants contained within said assay assembly to yield a detectable signal indicative of the presence of said analyte; and c) detecting said detectable signal. In another aspect, the method comprises the steps of a) providing a fluidic device comprising at least one sample collection unit, an immunoassay assembly containing immunoassay reagents, a plurality of channels in fluid communication with said sample collection unit and/or said immunoassay assembly; b) actuating said fluidic device and directing said immunoassay reagents within said fluidic device; c) allowing a sample of bodily fluid suspected to contain said analyte to react with said immunoassay reagents contained within said assay immunoassay assembly to yield a detectable signal indicative of the presence of said analyte indicative of an influenza viral infection in said sample; and d) detecting said detectable signal generated from said analyte collected in said sample of bodily fluid. Where desired, the sample of bodily fluid used for such detection is less than about 500 microliters. A variety of influenza viral infections can be detected. They include but are not limited to influenza type A, B, and C viral infection.

The present invention further provides a method of detecting a plurality of analytes, at least two of which are indicative of an influenza viral infection in a bodily fluid from a subject. The method comprise the steps of a) providing a fluidic device comprising at least one sample collection unit, an immunoassay assembly containing immunoassay reagents, a plurality of channels in fluid communication with said sample collection unit and/or said immunoassay assembly; b) actuating said fluidic device and directing said immunoassay reagents within said fluidic device; c) allowing a sample of bodily fluid suspected to contain said plurality of analytes to react with said immunoassay reagents contained within said assay immunoassay assembly to yield one or more detectable signals indicative of the presence of said at least two analytes in said sample; and d) detecting said one or more detectable signals generated from said plurality of analytes collected in said sample of bodily fluid.

Also provided in the present invention is a fluidic device for detecting a type of influenza viral infection. The fluidic devices comprise a cartridge comprising a plurality of reactants, at least two of which are reactive with different analytes present in a bodily fluid from a subject, wherein said different analytes are indicative of the type of influenza infection. In one aspect, each of the at least two reactants binds to a different surface glycoprotein of an influenza virus. The different surface glycoprotein may be a member selected from the group consisting of hemagglutinin and neuraminidase. Any two of the following surface glycoproteins can be the target analytes of the at least two reactants: hemagglutinin 1, hemagglutinin 2, hemagglutinin 3, hemagglutinin 4, hemagglutinin 5, hemagglutinin 6, hemagglutinin 7, hemagglutinin 8, hemagglutinin 9, hemagglutinin 10, hemagglutinin 11, hemagglutinin 12, hemagglutinin 13, hemagglutinin 14, hemagglutinin 15, hemagglutinin 16, neuraminidase 1, neuraminidase 2, neuraminidase 3, neuraminidase 4, and neuraminidase 5. In a preferred embodiment, one of the at least two reactants binds to hemagglutinin 5 and the other binds to neuraminidase 1. Where desired, the cartridge may further comprise a sample collection unit and an assay assembly. In some aspects, the assay assembly is an immunoassay assembly comprising immunoreactants.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
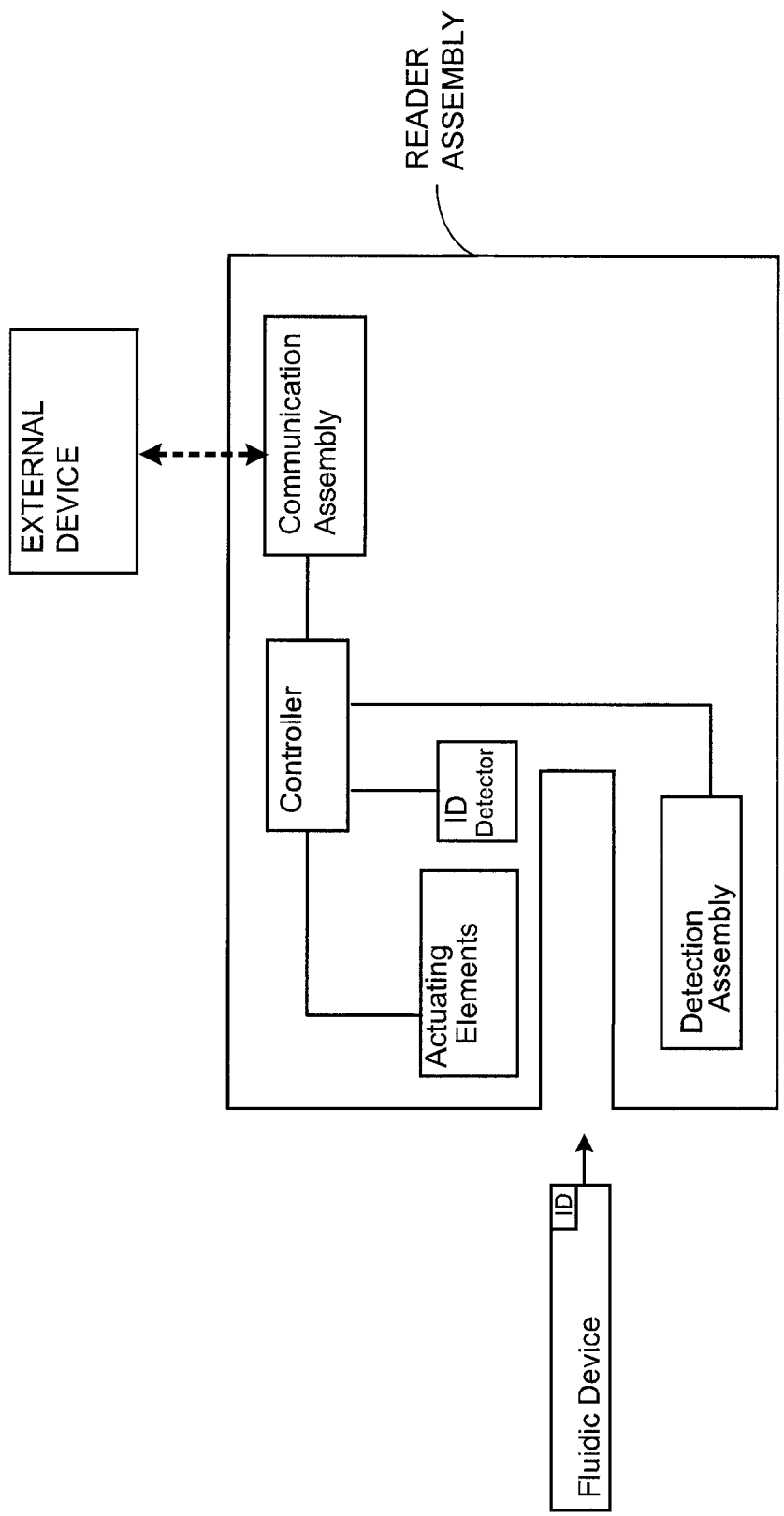
FIG. 1 is one embodiment showing multiple components of the present system.

One aspect of the present invention is a system for detecting an analyte indicative of an influenza viral infection present in a sample of bodily fluid. The analyte may be indicative of an influenza type A, type B, and/or type C viral infection. The analyte may comprise at least one surface glycoprotein of an influenza virus. Exemplary surface glycoproteins are, without limitation, hemagglutinins and neuraminidases. Hemagglutinin surface proteins include, but are not limited to, H1, H2, H3, H4, H5, H6, H7, H8, H9, H10, H11, H12, H13, H14, H15, and H16. Non-limiting neuraminidase surface proteins include N1, N2, N3, N4, and N5. The analyte may also comprise an antibody to a surface glycoprotein of an influenza virus that is generated by the infected host.

Another aspect of the present invention is a system for detecting a plurality of analytes, at least two of which are indicative of an influenza viral infection present in a sample of bodily fluid. Similarly, the analytes may be indicative of an influenza type A, type B, and/or type C viral infection. The analytes may comprise a plurality of surface glycoproteins of an influenza virus. In some embodiments, the plurality of surface glycoproteins comprises a hemagglutinin and a neuraminidase. The hemagglutinin may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5. In preferred embodiments the hemagglutinin is H5 and the neuraminidase is N1. The analytes may also be a plurality of antibodies specific for surface glycoproteins of an influenza virus. The system is capable of detecting and/or quantifying the analytes of particular interest.

One further aspect of the present invention is system for detecting a plurality of analytes incorporated into a single entity such as a viral particle or cell or cell fragment. In this aspect the plurality of analytes are preferably a combination of analytes, at least two of which are indicative of an influenza viral infection in a sample of bodily fluid. The analytes may be indicative of an influenza type A, type B, or type C viral infection. The plurality of analytes may comprise a combination of surface glycoproteins of an influenza virus. In some embodiments the plurality of analytes may be a combination of surface glycoproteins comprising a combination of a hemagglutinin and a neuraminidase. The hemagglutinin may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5. In preferred embodiments the combination of analytes is associated with a virulent strain of influenza such as the H5N1 combination. This aspect of the invention is specific for detecting the combination of the plurality of analytes. It can distinguish between infection with a virulent strain such as a combination of H5N1 and a putative-infection with a different combination of analytes. One variation of this aspect of the invention is to utilize one or more reactants reactive with one or more viral antigens (e.g., anti-viral surface glycoprotein antibody) to capture the viral particles at a reaction site, and then apply another set of reactant (either one or multiple reactants) to specifically detect for the bound viral particles. One exemplary set up will utilize anti-H2 antibodies as the capturing antibodies, and anti-N5 antibodies, preferably enzyme-labeled anti-N5 antibodies as the detecting reagent.

In some embodiments the system detects a plurality of human antibodies to viral antigens such as antibodies to surface glycoproteins of an influenza virus. These human antibodies can be circulating in the infected subjects.

In some embodiments the analyte of interest may be a complex of an analyte indicative of an influenza viral infection in a sample of bodily fluid and a human antibody to the analyte. The analyte may be any analyte indicative of an influenza viral infection described herein, but is preferably the H5 hemagglutinin, the N1 neuraminidase, or the H5N1 complex of the H5 and N1 surface glycoproteins.

A further aspect of the present invention is a system for detecting a plurality of analytes, wherein at least one analyte is indicative of an influenza viral infection in a sample of bodily fluid, and wherein at least one analyte is a biomarker in the sample of bodily fluid indicative of the stress imposed on the human body by the viral infection. The at least one analyte indicative of an influenza viral infection may be any analyte indicative of an influenza viral infection described herein. Exemplary biomarkers indicative of the stress imposed on the human body by the viral infection include, without limitation, CRP, TNFα, interleukins and the like.

The subject system typically comprises a fluidic device having one or more of the following components: a sample collection unit, an assay assembly, a reader assembly, and a communication assembly. The sample collection unit typically allows a sample of bodily fluid collected from a subject to react with reactants contained within the assay assembly for generating a signal indicative of the presence of the analyte of interest. The reader assembly detects the signal, which is then transmitted via the communication assembly to an external device for further processing.

Any bodily fluids suspected to contain an analyte of interest can be used in conjunction with the subject system or devices. Commonly employed bodily fluids include but are not limited to blood, plasma, blood serum, saliva, urine, gastric and digestive fluid, tears, stool, semen, vaginal fluid, interstitial fluids and cerebrospinal fluid. In a preferred embodiment, the bodily fluids are used directly for detecting the analytes present therein with the subject fluidic device without further processing. Where desired, however, the bodily fluids can be pre-treated before performing the analysis with the subject fluidic devices. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the analyte is a molecule present on or within a cell, extraction can be performed using lysing agents including but not limited to denaturing detergent such as SDS or non-denaturing detergent such as Thesit®, sodium deoxycholate, Triton®X-100, and TWEEN®20. In some embodiments sample pretreatment is accomplished automatically within the fluidic device.

The volume of bodily fluid to be used with a fluidic device of the present invention is generally less than about 500 microliters, typically between about 1 to 100 microliters. Where desired, a sample of 1 to 50 microliters or 1 to 10 microliters can be used for detecting an analyte using the subject fluidic device.

A benefit of the current invention is that only a very small volume of blood is required to detect an analyte of interest in animals. In some embodiments between about 1 microliter and about 50 microliters are drawn. In preferred embodiment between about 1 microliter and 10 microliters are drawn. In preferred embodiments about 5 microliters of blood are drawn from the subject.

A bodily fluid may be drawn from a subject and brought into the fluidic device in a variety of ways, including but not limited to, lancing, injection, or pipetting. In one embodiment, a lancet punctures the skin and draws the sample into the fluidic device using, for example, gravity, capillary action, aspiration, or vacuum force. The lancet may be part of the fluidic device, or part of a reader assembly, or as a stand alone component. Where needed, the lancet may be activated by a variety of mechanical, electrical, electromechanical, or any other known activation mechanism or any combination of such methods. In another embodiment where no active mechanism is required, a subject can simply provide a bodily fluid to the fluidic device, as for example, could occur with a saliva sample. The collected fluid can be placed in the sample collection unit within the fluidic device. In yet another embodiment, the fluidic device comprises at least one microneedle which punctures the skin. The microneedle can be used with a fluidic device alone, or can puncture the skin after the fluidic device is inserted into a reader assembly.

In some embodiments a microneedle is about the size of a human hair and has an integrated microreservoir or cuvette. The microneedle may painlessly penetrate the skin of a subject and draw a small blood sample. More preferably, the microneedle collects about 0.01 to about 1 microliter, preferably about 0.05 to about 0.5 microliters and more preferably about 0.1 to about 0.3 microliters of capillary blood. In some embodiments a microneedle may be constructed out of silicon and is about 10 to about 200 microns in diameter, preferably about 50 to about 150 microns in diameter, and most preferably about 100 microns in diameter, making their application to the skin virtually painless. To ensure that a capillary is actually struck by a needle, a plurality of microneedles may be used for sample collection. Such microneedles may be of the type marketed by Pelikan (Palo Alto, Calif.) and/or Kumetrix (Union City, Calif.). U.S. Pat. No. 6,503,231 discloses microneedles which may be used with the present invention.

Microfabrication processes that may be used in making the microneedles disclosed herein include without limitation lithography; etching techniques such as wet chemical, dry, and photoresist removal; thermal oxidation of silicon; electroplating and electroless plating; diffusion processes such as boron, phosphorus, arsenic, and antimony diffusion; ion implantation; film deposition such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). Alternatively, microneedles may be molded in silicon wafers and then plated using conventional wire cutting techniques with nickel, gold, titanium or various other biocompatible metals. In some embodiments microneedles can be fashioned from biopolymers. In some embodiments microneedles may be fabricated and employed for the claimed devices according to the methods of Mukerjee et al., Sensors and Actuators A: Physical, Volume 114, Issues 2-3, 1 Sep. 2004, Pages 267-275.

In preferred embodiments a microneedle is only used once and then discarded. In some embodiments a mechanical actuator can insert and withdraw the microneedle from the subject, discard the used needle, and reload a new microneedle. The mechanical technologies developed and manufactured in very high volumes for very small disk drives have a similar set of motion and low cost requirements. In preferred embodiments the actuator is a MEMS (micro machined electromechanical system) device fabricated using semiconductor-like batch processes. Such actuators include without limitation nickel titanium alloy, neumatic, or piezo electric devices. In some embodiments the microneedles are about 1 micron to about 10 microns in thickness, preferably about 2 microns to about 6 microns in thickness, and most preferably about 4 microns in thickness. In some embodiments the microneedles are about 10 microns to about 100 microns in height, preferably about 30 microns to about 60 microns in height, and most preferably about 40 microns in height.

FIG. 1 illustrates an exemplary system of the present invention. As illustrated, a fluidic device provides a bodily fluid from a subject and can be inserted into a reader assembly. The fluidic device may take a variety of configurations and in some embodiments the fluidic device may be in the form of a cartridge. An identifier (ID) detector may detect an identifier on the fluidic device. The identifier detector communicates with a communication assembly via a controller which transmits the identifier to an external device. Where desired, the external device sends a protocol stored on the external device to the communication assembly based on the identifier. The protocol to be run on the fluidic device may comprise instructions to the controller of the reader assembly to perform the protocol on the fluidic device, including but not limited to a particular assay to be run and a detection method to be performed. Once the assay is performed on the fluidic device, a signal indicative of an analyte indicative of an influenza viral infection in the bodily fluid sample is generated and detected by a detection assembly. The detected signal may then be communicated to the communications assembly, where it can be transmitted to the external device for processing, including without limitation, calculation of the analyte concentration in the sample or determination of the presence of the analyte.

Figure 2:
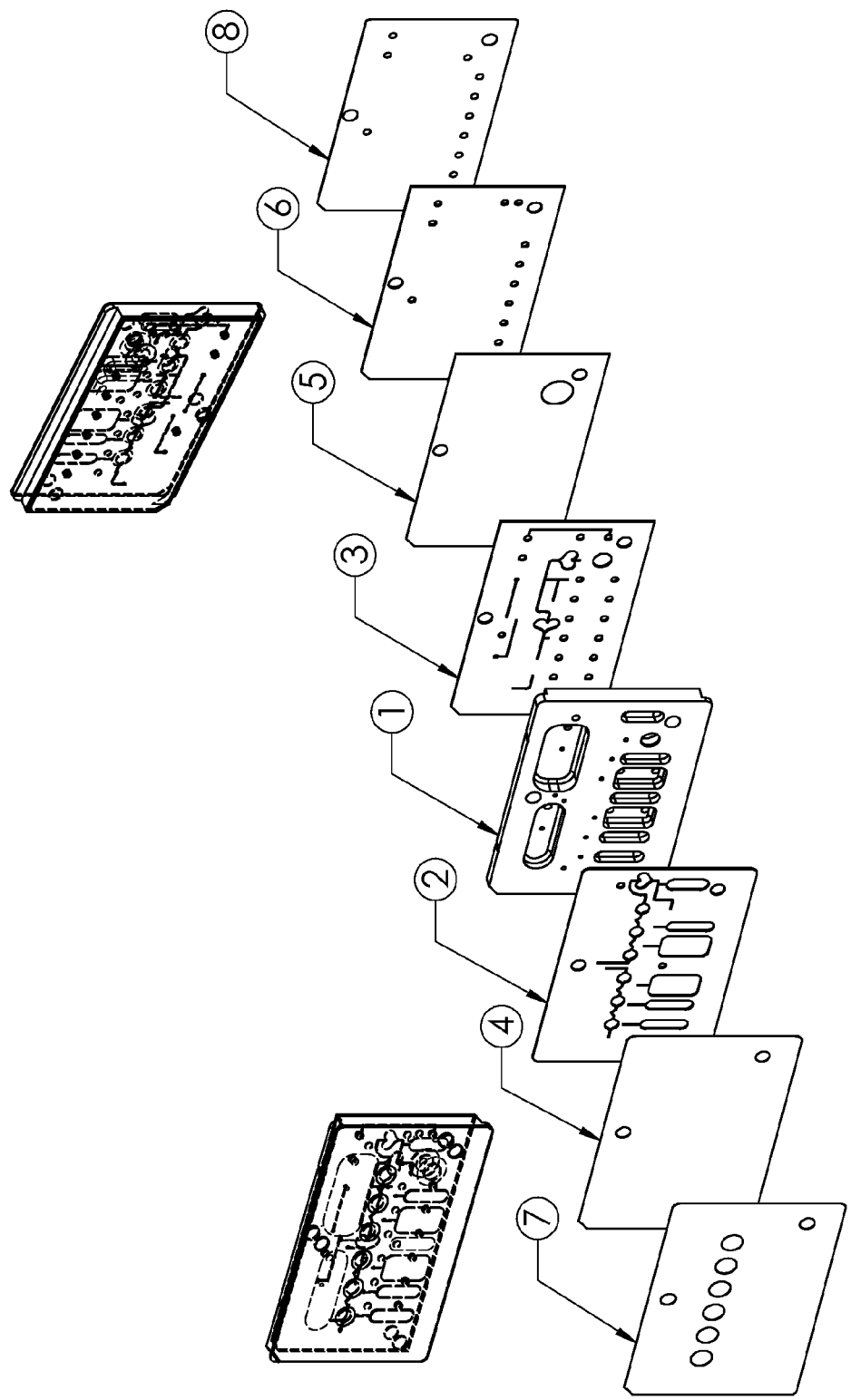
FIG. 2 shows different layers of an exemplary fluidic device prior to assembly.
Figure 3:
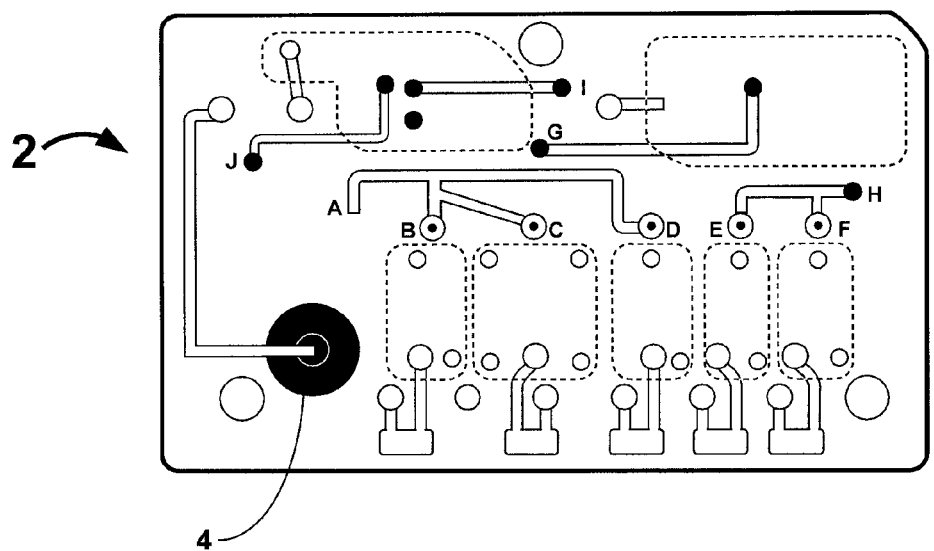
FIGS. 3 and 4 illustrate the fluidic network within an exemplary fluidic device.
Figure 4:
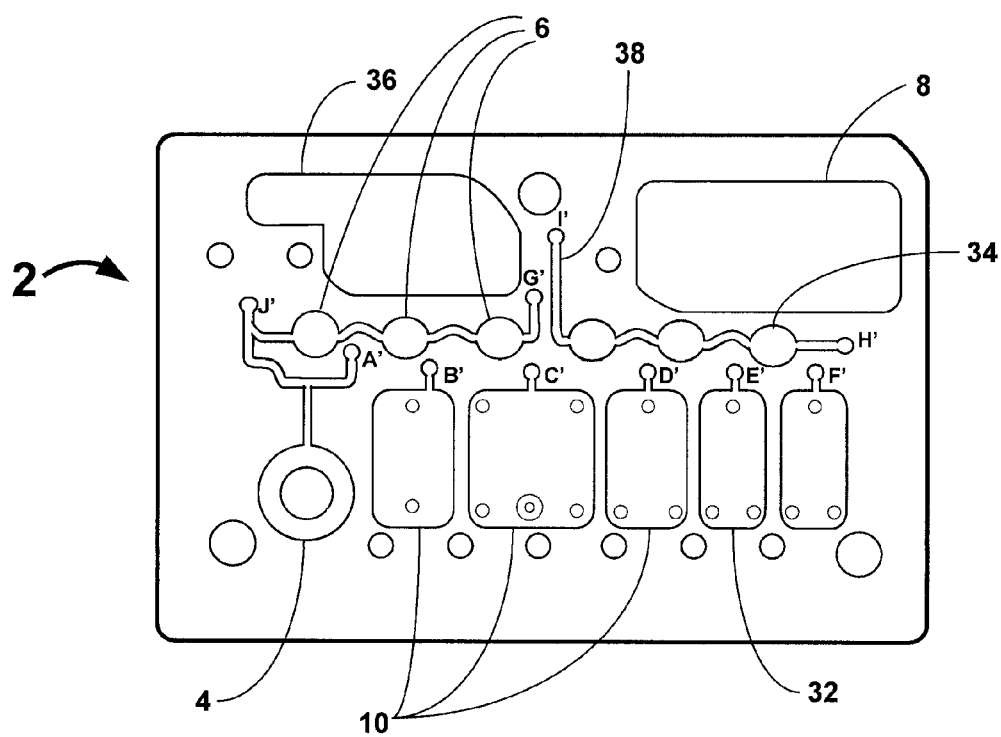

FIG. 2 illustrates exemplary layers of a fluidic device according to the present invention prior to assembly of the fluidic device which is disclosed in more detail below. FIGS. 3 and 4 show a top and bottom view, respectively, of an exemplary fluidic device after the device has been assembled. The different layers are designed and assembled to form a three dimensional fluidic channel network. A sample collection unit 4 provides a sample of bodily fluid from a subject. As will be explained in further detail below a reader assembly comprises actuating elements (not shown) can actuate the fluidic device to start and direct the flow of a bodily fluid sample and assay reagents in the fluidic device. In some embodiments actuating elements first cause the flow of sample in the fluidic device 2 from sample collection unit 4 to reaction sites 6, move the sample upward in the fluidic device from point G' to point G, and then to waste chamber 8. The actuating elements then initiate the flow of reagents from reagent chambers 10 to point B', point C', and point D', then upward to points B, C, and D, respectively, then to point A, down to point A', and then to waste chamber 8 in the same manner as the sample.

A sample collection unit 4 in a fluidic device 2 may provide a bodily fluid sample from a subject by any of the methods described above. If necessary, the sample may first be processed by diluting the bodily fluid in a dilution chamber, and or may be filtered by separating the plasma from the red blood cells in a filtration chamber. In some embodiments the sample collection unit, diluting chamber, and filtration chamber may be the same component, and in some embodiments they may be different components, or any two may be the same component and the other may be a separate component. In some embodiments there may be more than one sample collection unit in the fluidic device.

In some embodiments it may be desirable to detect the presence of analytes on a cell or viral surface, within a cell or viral membrane, or inside a cell. The difficulty of detecting such analytes is that cells and other formed elements are particulate and components of cells do not readily interact with traditional assay chemistries which are designed to operate on analytes in solution. Cell-surface analytes react slowly and inefficiently with surface bound probes, and analytes inside the cell may not react at all with bound probes. To allow the detection of such analytes, in some embodiments the fluidic device may include a lysing assembly to lyse cells present in the bodily fluid sample. The lysing assembly may be incorporated with the sample collection unit, a dilution chamber, and/or a filtration chamber. In some embodiments the sample collection unit, dilution chamber, and lysing component are within the same element in the fluidic device. In some embodiments the lysing component may be incorporated with an assay reagent described below.

Where desired, lysing agents may be impregnated and then dried into porous mats, glass fiber mats, sintered fits or particles such as Porex, paper, or other similar material. Lysing agents may be dried onto flat surfaces. Lysing agents may also be dissolved in liquid diluents or other liquid reagents. In preferred embodiments porous materials are used to store the lysing agents because they can store a lysing agent in dry form likely to be very stable. They also facilitate the mixing of the bodily fluid sample with the lysing agent by providing a tortuous path for the sample as it moves through the porous material. In preferred embodiments such porous materials have a disc shape with a diameter greater than its thickness. In some embodiments lysing agents may be dried onto porous materials using lyophilization, passive evaporation, exposure to warm dry flowing gas, or other known methods.

A variety of lysing agents are available in the art and are suitable for use in connection with the subject fluidic device. Preferred lysing agents are non-denaturing, such as non-denaturing detergents. Non-limiting examples of non-denaturing detergents include Thesit®, sodium deoxycholate, Triton®X-100, and TWEEN®20. The agents are preferably non-volatile in embodiments where the agents are impregnated into a solid porous materials. In some embodiments lysing agents are mixed together. Other materials may be mixed with the lysing agents to modify the lytic effects. Such exemplary materials may be, without limitation, buffers, salts, and proteins. In preferred embodiments lysing agents will be used in amounts that are in excess of the minimum amount required to lyse cells. In some embodiments lysing agents will be used that can lyse both white and red cells.

One of the advantages of the present invention is that any reagents necessary to perform an assay on a fluidic device according to the present invention are preferably on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

In a preferred embodiment there is at least one reagent chamber. In some embodiments there may be two, three, four, five, six, or more, or any number of reagent chambers as are necessary to fulfill the purposes of the invention. A reagent chamber is preferably in fluid communication with at least one reaction site, and when the fluidic device is actuated as described herein, reagents contained in said reagent chambers are released into the fluidic channels within the fluidic device.

Reagents according to the present invention include without limitation wash buffers, enzyme substrates, dilution buffers, conjugates, enzyme-labeled conjugates, sample diluents, wash solutions, sample pre-treatment reagents including additives such as detergents, polymers, chelating agents, albumin-binding reagents, enzyme inhibitors, enzymes, anti-coagulants, red-cell agglutinating agents, antibodies, or other materials necessary to run an assay on a fluidic device. An enzyme conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments the reagents comprise immunoassay reagents.

In some embodiments a reagent chamber contains approximately about 50 µl to about 1 ml of fluid. In some embodiments the chamber may contain about 100 µl of fluid. The volume of liquid in a reagent chamber may vary depending on the type of assay being run or the sample of bodily fluid provided. In some embodiments the reagents are initially stored dry and liquefied (e.g., dissolved or melted) upon initiation of the assay being run on the fluidic device.

Figure 5:
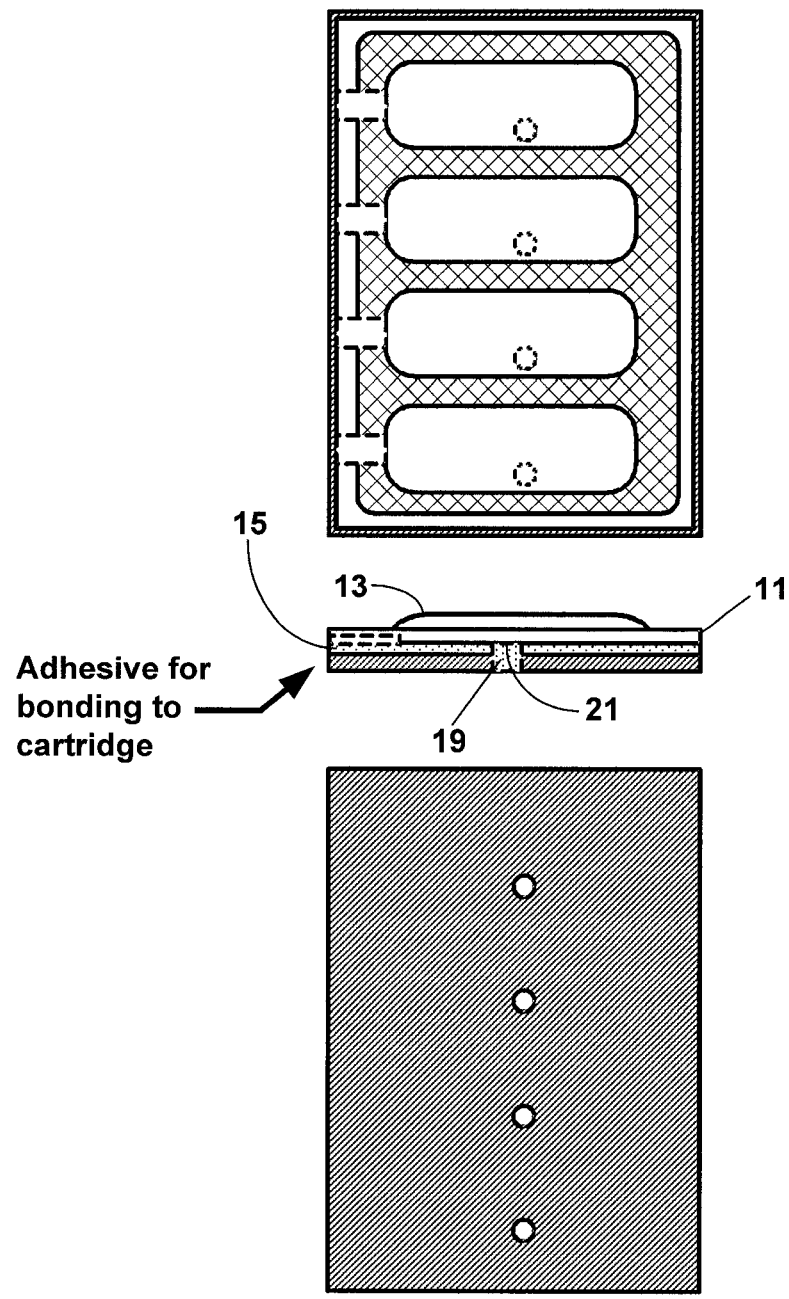
FIG. 5 shows a top, side, and bottom view of exemplary reagent chambers of the present invention.
Figure 6:
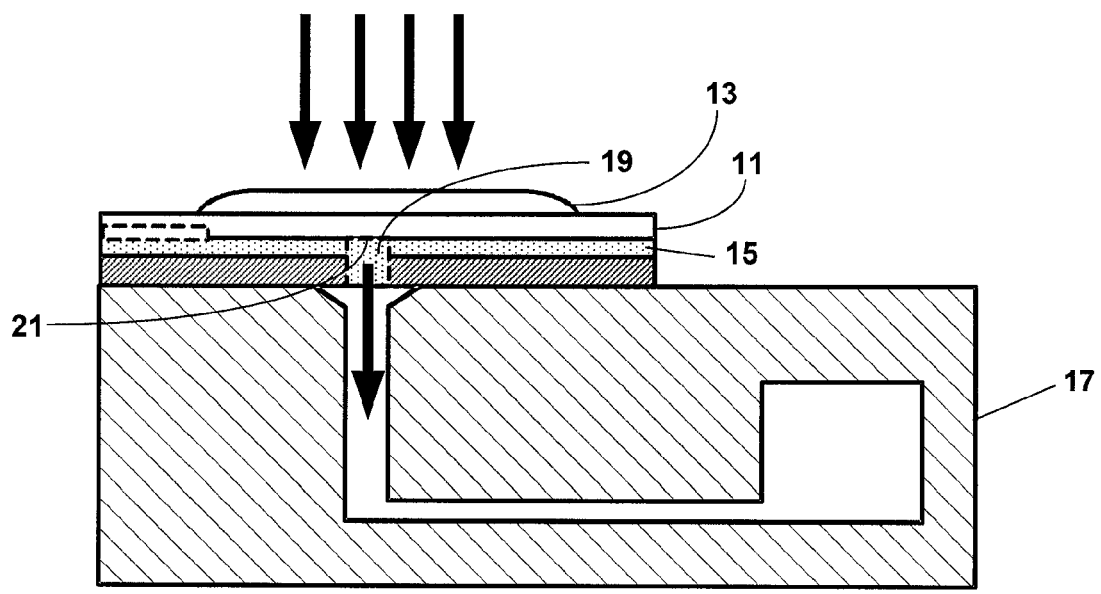
FIG. 6 illustrates an exemplary side view of a reagent chamber in fluidic communication with a fluidic device.

FIGS. 5 and 6 illustrate an exemplary embodiment of a sealed reagent chamber. FIG. 5 shows a top, side, and bottom view of a reagent chamber. A top layer 11 contains a plurality of blisters or pouches 13. A bottom layer 15 has a bottom surface that is bonded to the fluidic device base 17 as shown in FIG. 6. The bottom layer 15 has a plurality of fluidic channels 19 dispersed through the entire surface, where each channel traverses the bottom layer 15. The fluid in the reagent chamber is contained within the chamber by pressure burstable seal 21 between the fluidic channel 19 and the chamber 13. The burstable seal 21 is designed such that at a pre-determined pressure the seal bursts allowing the fluid in the chamber 13 to flow out into a fluidic channel 19.

Figure 7:
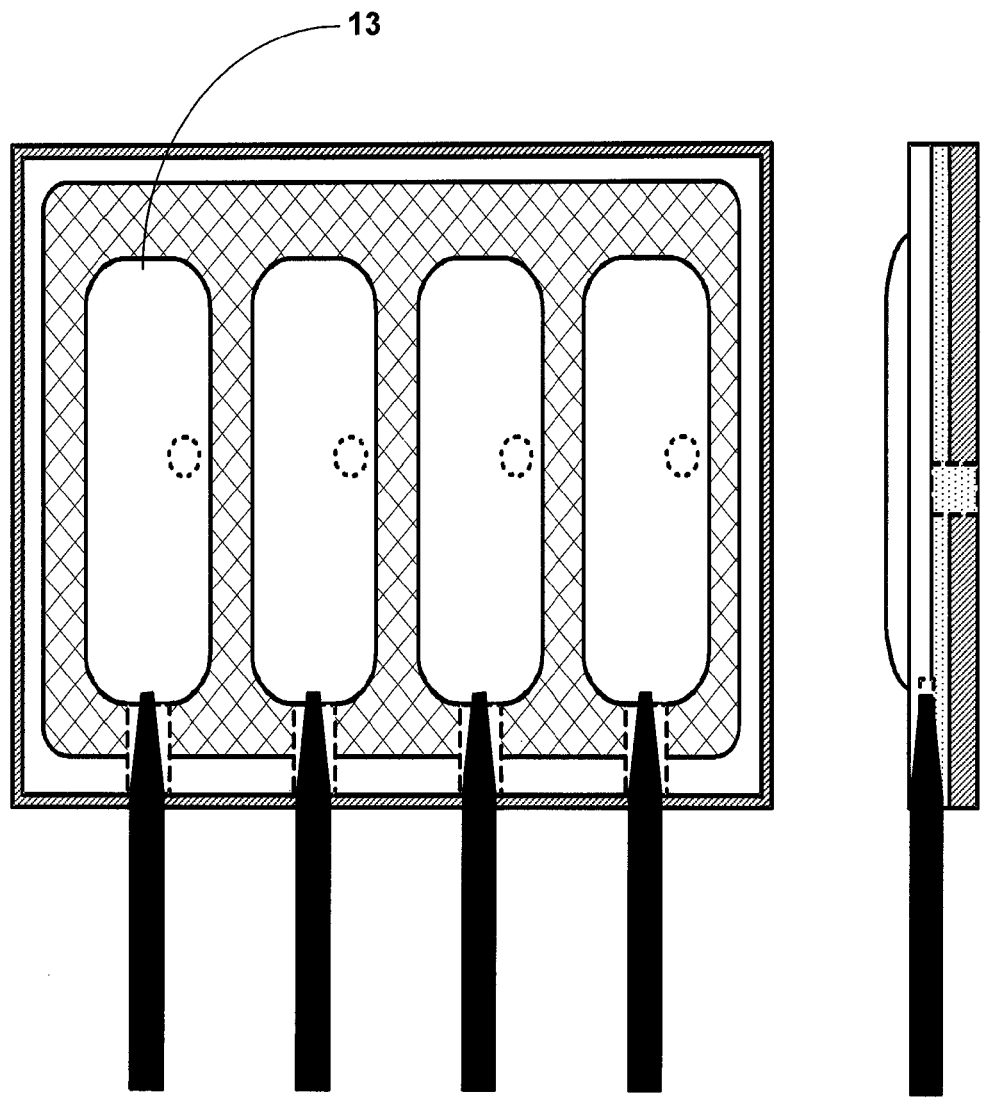
FIG. 7 illustrates exemplary reagent chambers being filled with reagents.

FIG. 7 shows an exemplary process of filling the reagent chambers 13 with, for example, reagents. Reagent chambers 13 may be filled with fluid using a fill channel and a vacuum draw channel. The process of filling the reagents involves first removing all the air from the chamber. This is done by drawing a vacuum through the vacuum draw channel. Once the vacuum is drawn, a permanent seal is placed between the fill channel and the vacuum draw channel. Next, required reagents are dispensed into the chamber through the fill channel. Then, a permanent seal is placed between the chamber and the fill channel. This ensures that when the chamber is compressed, the fluid can flow in only one direction, towards the burstable seal. If the compression imparts a pressure larger than the burst pressure of seal, the seal bursts and the fluid flows into the fluidic channel.

Figure 8:
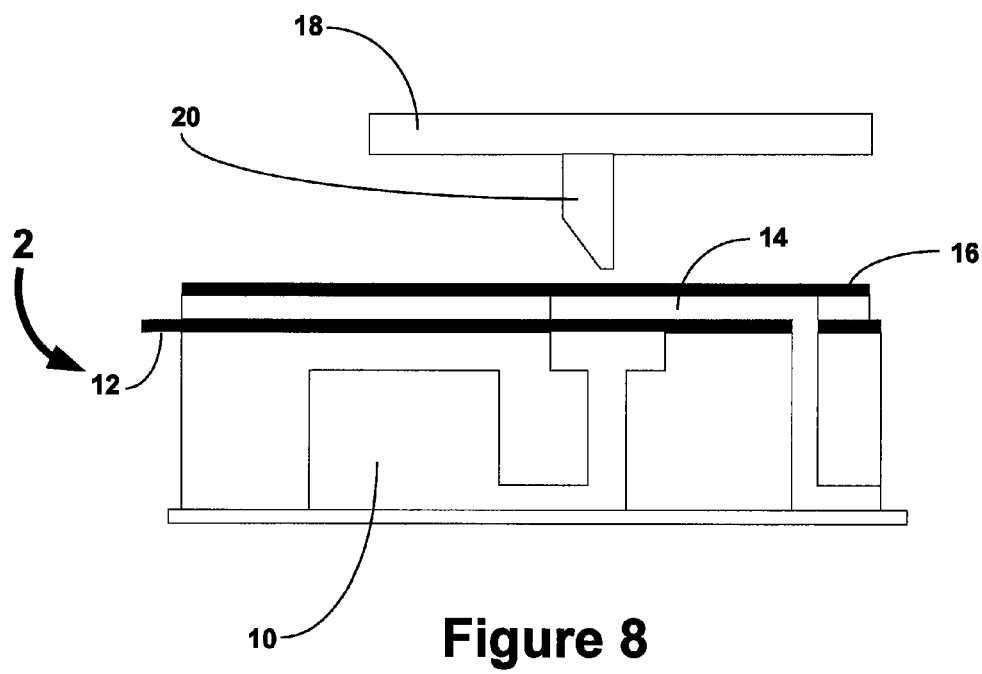
FIGS. 8 and 9 illustrate a side view of an exemplary fluidic device is combination with actuating elements of the reader assembly.
Figure 9:
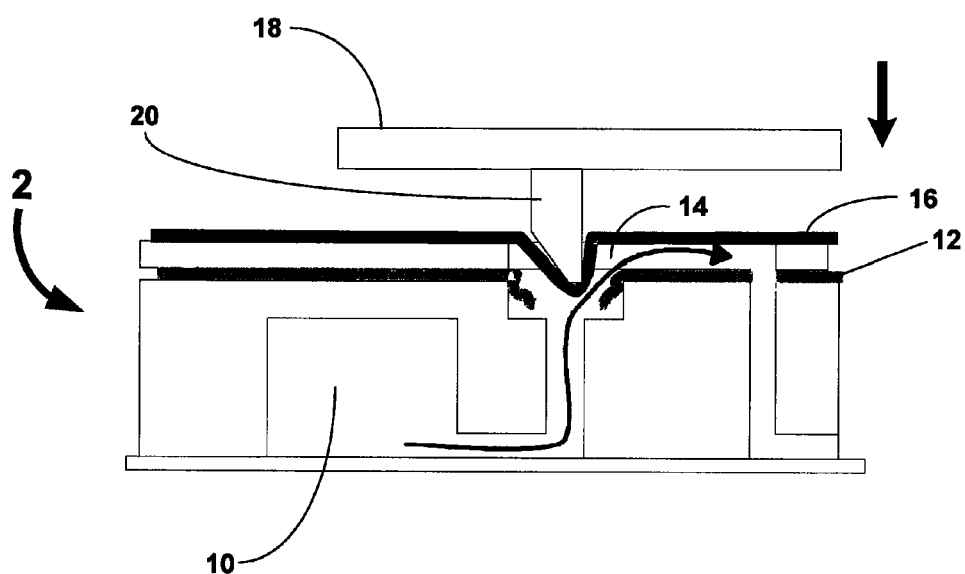

FIGS. 8 and 9 illustrate an embodiment of a fluidic device in operation with actuating elements as described herein. Fluidic device 2 contains a reagent chamber 10 and a layer of burstable foil 12 enclosing the reagent chamber. Above the burstable foil 12 is a portion of the microfluidic circuit 14. A tough, but elastomeric top cover 16 acts as the top layer of the fluidic device 2. The reader assembly includes a valve actuation plate 18. Securely attached to the plate 18 is a non-coring needle 20 such that when the plate is lowered, the sharp edge of the needle contacts the elastomeric cover 16. The top cover could also be made of flexible silicone material that would act as a moisture impermeable seal. This embodiment also provides a solution to liquid evaporation and leakage from a fluidic device by isolating any liquid reagents in the fluidic device from any dry reagents until the assay is initiated.

In preferred embodiments the reagent chamber and sample collection unit are fluidly connected to reaction sites where bound probes can detect an analyte of interest in the bodily fluid sample using the assay. A reaction site could then provide a signal indicative of the presence of the analyte of interest, which can then be detected by a detection device described in detail herein below.

In some embodiments the reactions sites are flat but they may take on a variety of alternative surface configurations. The reaction site preferably forms a rigid support on which a reactant can be immobilized. The reaction site surface is also chosen to provide appropriate light-absorbing characteristics. For instance, the reaction site may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. Other appropriate materials may be used in accordance with the present invention.

A reactant immobilized at a reaction site can be anything useful for detecting an analyte of interest in a sample of bodily fluid. For instance, such reactants include without limitation, antibodies, cell membrane receptors, monoclonal antibodies and antisera reactive with a specific analyte indicative of an influenza viral infection. Various commercially available reactants such as a host of polyclonal and monoclonal antibodies specifically developed for specific analytes can be used.

A preferred class of reactants are antibodies. As used herein, an "antibody" (interchangeably used in plural form) is an immunoglobulin molecule capable of specific binding to a target, such as an analyte in a bodily fluid, through at least one antigen recognition site, located in the variable region of the immunoglobulin molecule. As used herein, the term encompasses not only intact antibodies, but also fragments thereof (such as Fab, Fab', F(ab')$_2$, Fv, single chain (ScFv), mutants thereof, fusion proteins, humanized antibodies, and any other modified configuration of the immunoglobulin molecule that comprises an antigen recognition site of the required specificity.

The subject methods and apparatus can utilize antibody reactants that are commercially available or generated de novo. Laboratory methods for producing polyclonal antibodies and monoclonal antibodies, are known in the art. For example, see Harlow and Lane, *Antibodies: A Laboratory Manual*, Cold Spring Harbor Laboratory, New York (1988) and Sambrook et al. (1989). Briefly, monoclonal antibodies useful for the present invention can be biologically produced by introducing an antigen of an influenza virus into an animal, e.g., mouse or rat. The antibody producing cells in the animal are isolated and fused with myeloma cells or heteromyeloma cells to produce hybrid cells or hybridomas.

Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307.

The antibody reactants can be linked (i.e., conjugated) to a suitable detectable label depending on the particular assay reaction.

In some embodiments a reactant detects an analyte indicative of an influenza type A, type B, or type C viral infection. The analyte may comprise at least one surface glycoprotein of an influenza virus. Exemplary surface glycoproteins are, without limitation, a hemagglutinin and a neuraminidase. Hemagglutinin surface proteins include H1, H2, H3, H4, H5, H6, H7, H8, H9, H10, H11, H12, H13, H14, H15, and H16. Neuraminidase surface proteins include N1, N2, N3, N4, and N5.

In some embodiments the reactants detect a plurality of analytes, at least two of which are indicative of an influenza viral infection in a sample of bodily fluid. The analytes may be indicative of an influenza type A, type B, or type C viral infection. The analytes may comprise a plurality of surface glycoproteins of an influenza virus. In some embodiments the plurality of surface glycoproteins comprises a hemagglutinin and a neuraminidase. The hemagglutinin may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5. In preferred embodiments the hemagglutinin is H5 and the neuraminidase is N1.

One skilled in the art will appreciate that there are many ways of immobilizing various reactants onto a support where reaction can take place. The immobilization may be covalent or noncovalent, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art.

In some embodiments there are more than one reaction sites which can allow for detection of multiple analytes of interest from the same sample of bodily fluid. In some embodiments there are 2, 3, 4, 5, 6, or more reaction sites, or any other number of reaction sites as may be necessary to carry out the intent of the invention.

In embodiments with multiple reaction sites on a fluidic device, each reaction site may be immobilized with a reactant different from a reactant on a different reaction site. In a fluidic device with, for example, three reaction sites, there may be three different probes, each bound to a different reaction site to bind to three different analytes of interest in the sample. In some embodiments there may be different reactants bound to a single reaction site if, for example, a CCD with multiple detection areas were used as the detection device, such that multiple different analytes could be detected in a single reaction site. The capability to use multiple reaction sites in addition to multiple different probes on each reaction site enables the high-throughput characteristics of the present invention.

In preferred embodiments of the invention the fluidic device includes at least one waste chamber to trap or capture all liquids after they have been used in the assay. In preferred embodiments, there is more than one waste chamber, at least one of which is to be used with a calibration assembly described herein below. On-board waste chambers also allow the device to be easily disposable. The waste chamber is preferably in fluidic communication with at least one reaction site.

At least one of these channels will typically have small cross sectional dimensions. In some embodiments the dimensions are from about 0.01 mm to about 5 mm, preferably from about 0.03 mm to about 3 mm, and more preferably from about 0.05 mm to about 2 mm Fluidic channels in the fluidic device may be created by, for example without limitation, precision injection molding, laser etching, or any other technique known in the art to carry out the intent of the invention.

To ensure that a given assay response (e.g. a photon count) produced at a reaction site correlates with an accurate concentration of an analyte of interest in a sample, it is preferably advantageous to calibrate the fluidic device before detecting the response (e.g., detecting photons). Calibrating a fluidic device at the point of manufacturing for example may be insufficient to ensure an accurate analyte concentration is determined because a fluidic device may be shipped prior to use and may undergo changes in temperature, for example, so that a calibration performed at manufacturing does not take into effect any subsequent changes to the structure of the fluidic device or reagents contained therein. In a preferred embodiment of the present invention, a fluidic device has a calibration assembly that mimics the assay assembly in components and design except that a sample is not introduced into the calibration assembly. Referring to FIGS. 3 and 4, a calibration assembly occupies about half of the fluidic device 2 and includes reagent chambers 32, reactions sites 34, a waste chamber 36, and fluidic channels 38. Similar to the assay assembly, the number of reagent chambers and reaction sites may vary depending on the assay being run on the fluidic device and the number of analytes being detected.

Where desired, a sensor for assessing the reliability of an assay for an analyte in a bodily fluid with the use of the subject fluidic device can be provided together with the fluidic device, the reader and/or within the packaging of the subject system. The sensor is capable of detecting a change in operation parameters under which the subject system normally operates. The operation parameters include but are not limited to temperature, humidity, and pressure, which may affect the performance of the present system.

A fluidic device and reader assembly may, after manufacturing, be shipped to the end user, together or individually. As a reader assembly is repeatedly used with multiple fluidic devices, it may be necessary to have sensors on both the fluidic device and reader assembly to detect such changes during shipping, for example. During shipping, pressure or temperature changes can impact the performance of a number of components of the present system, and as such a sensor located on either the fluidic device or reader assembly can relay these changes to, for example, the external device so that adjustments can be made during calibration or during data processing on the external device. For example, if the pressure or temperature of a fluidic device reached a certain level during shipping, a sensor located on the fluidic device could detect this change had occurred and convey this information to the reader assembly when it is inserted into the reader assembly by the user. There may be an additional detection device in the reader assembly to perform this, or such a device may be incorporated into another system component. In some embodiments this information may be wirelessly transmitted to either the reader assembly or the external device. Likewise, a sensor in the reader assembly can detect similar changes. In some embodiments, it may be desirable to have a sensor in the shipping packaging as well, either instead of in the system components or in addition thereto.

Manufacturing of the fluidic channels may generally be carried out by any number of microfabrication techniques that are well known in the art. For example, lithographic techniques are optionally employed in fabricating, for example, glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding or stamp molding methods where large numbers of substrates are optionally produced using, for example, rolling stamps to produce large sheets of microscale substrates or polymer microcasting techniques where the substrate is polymerized within a micromachined mold.

In some embodiments at least one of the different layers of the fluidic device may be constructed of polymeric substrates. Non limiting examples of polymeric materials include polystyrene, polycarbonate, polypropylene, polydimethysiloxanes (PDMS), polyurethane, polyvinylchloride (PVC), and polysulfone.

The fluidic device may be manufactured by stamping, thermal bonding, adhesives or, in the case of certain substrates, for example, glass, or semi-rigid and non-rigid polymeric substrates, a natural adhesion between the two components. In some embodiments the fluidic device is manufactured by ultrasonic or acoustic welding.

FIG. 2 shows one embodiment of the invention in which fluidic device 2 is comprised of 7 layers. Features as shown are, for example, cut in the polymeric substrate such that when the layers are properly positioned when assembly will form a fluidic network. In some embodiments more or fewer layers may be used to construct a fluidic device to carry out the purpose of the invention.

One objective of the present invention is to prevent fluid inside a fluidic device from contacting the components of a reader assembly which may need to remain dry and or uncontaminated, and also to prevent contamination to a detection device within the reader assembly. A leak in the fluidic device could result in liquids, for example reagents or waste, escaping from the fluidic device and contaminating the reader. In other embodiments a liquid absorbing material, such as polymeric materials found in diapers, could be placed within a portion of the fluidic channel or waste chamber to absorb the waste liquid. A non-limiting example of such a polymer is sodium polyacrylate. Such polymers can absorb fluids hundreds of times their weight. Hence, only minute quantities of such polymeric materials may be required to accomplish the goal of absorbing leaked fluids. In some embodiments a waste chamber is filled with a superabsorbent material. In some embodiments leaked liquid may be converted into a gel or other solid or semi-solid form.

Another objective of the present system is to provide a fluidic device that can run a variety of assays on a fluidic device. A protocol dependent on the identity of the fluidic device may be transferred from an external device where it can be stored to a reader assembly to enable the reader assembly to carry out the specific protocol on the fluidic device. In preferred embodiments, the fluidic device has an identifier (ID) that is detected or read by an identifier detector described herein. The identifier can then be communicated to a communication assembly, where it can then be transferred or transmitted to an external device.

In some embodiments the identifier may be a bar code identifier with a series of black and white lines, which can be read by an identifier detector such as a bar code reader, which are well known. Other identifiers could be a series of alphanumerical values, colors, raised bumps, or any other identifier which can be located on a fluidic device and be detected or read by an identifier detector. In some embodiments the identifier may comprise a storage or memory device and can transmit information to an identification detector. In some embodiments both techniques may be used.

Once a bodily fluid sample is provided to a fluidic device, it is inserted in a reader assembly. In some embodiments the fluidic device is partially inserted manually, and then a mechanical switch in the reader assembly automatically properly positions the fluidic device inside the reader assembly. Any other mechanism known in the art for inserting a disk or cartridge into a device may be used as well. In some embodiments only manual insertion may be required.

In some embodiments the reader assembly comprises an identifier detector for detecting or reading an identifier on the fluidic device, a controller for automatically controlling the detection assembly and also mechanical components of the reader assembly, for example, pumps and/or valves for controlling or directing fluid through the fluidic device, a detection device for detecting a signal created by an assay run on the fluidic device, and a communication assembly for communicating with an external device.

An identifier detector detects an identifier on the fluidic device which is communicated to a communication assembly. In some embodiments the identifier detector can be a bar code scanner-like device, reading a bar code on a fluidic device. The identifier detector may also be an LED that emits light which can interact with an identifier which reflects light and is measured by the identifier detector to determine the identity of a fluidic device.

In preferred embodiments the reader assembly houses a controller which controls a pump and a series of valves to control and direct the flow of liquid within the fluidic device. In some embodiments the reader assembly may comprises multiple pumps. The sample and reagents are preferably pulled through the fluidic channels by a vacuum force created by sequentially opening and closing at least one valve while activating a pump within the reader assembly. Methods of using at least one valve and at least one pump to create a vacuum force are well known. While a negative pulling force may be used, a positive pushing force may also be generated by at least one pump and valve according to the present invention. In other embodiments movement of fluid on the fluidic device may be by electro-osmotic, capillary, piezoelectric, or microactuator action.

FIGS. 8 and 9 illustrate an exemplary sequence to initiate the flow of a reagent within the fluidic device. An actuation plate 18 in the reader assembly comprises a non-coring needle or pin 20 which when lowered flexes the top cover 16, as it is preferably made of strong, flexible elastomeric material. However, the easily rupturable foil 12 then ruptures due to the stress induced by the flexing of top cover 16. Valves located downstream to the reagent chamber puncture different areas of foil in the fluidic device and can then work in tandem with a pump within the reader assembly to create a vacuum force to pull the reagent out of the reagent chamber 6 into a fluidic channel and then direct the flow of the reagent to a reaction site. At least one valve is preferably fluidically connected to a pump housed within the reader assembly. The non-coring needle or pin 20 is removed from the fluidic device when the device is removed from the reader assembly. One of the advantages of this embodiment is that no on-chip pump is required, which, at least, decreases the size and cost of the fluidic device, and allows the device to be disposable.

A reaction assembly preferably houses a detection assembly for detecting a signal produced by at least one assay on the fluidic device. FIG. 1 illustrates an exemplary position of a detection device of the present invention in relation to the fluidic device which is below the fluidic device. The detection assembly may be above the fluidic device or at a different orientation in relation to the fluidic device based on, for example, the type of assay being performed and the detection mechanism being employed.

In preferred embodiments an optical detector is used as the detection device. Non-limiting examples include a photodiode, photomultiplier tube (PMT), photon counting detector, or charge-coupled device (CCD). In some embodiments a pin diode may be used. In some embodiments a pin diode can be coupled to an amplifier to create a detection device with a sensitivity comparable to a PMT. Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

In some embodiments, the detection system may comprise non-optical detectors or sensors for detecting a particular parameter of a subject. Such sensors may include temperature, conductivity, potentiometric, and amperometric, for compounds that are oxidized or reduced, for example, $O_2$, $H_2O_2$, and $I_2$, or oxidizable/reducible organic compounds.

A communication assembly is preferably housed within the reader assembly and is capable of transmitting and receiving information wirelessly from an external device. Such wireless communication may be bluetooth or RTM technology. Various communication methods can be utilized, such as a dial-up wired connection with a modem, a direct link such as a T1, ISDN, or cable line. In preferred embodiments a wireless connection is established using exemplary wireless networks such as cellular, satellite, or pager networks, GPRS, or a local data transport system such as Ethernet or token ring over a local area network. In some embodiments the information is encrypted before it is transmitted over a wireless network. In some embodiments the communication assembly may contain a wireless infrared communication component for sending and receiving information.

In some embodiments the communication assembly can have a memory or storage device, for example localized RAM, in which the information collected can be stored. A storage device may be required if information can not be transmitted at a given time due to, for example, a temporary inability to wirelessly connect to a network. The information can be associated with the fluidic device identifier in the storage device. In some embodiments the communication assembly can retry sending the stored information after a certain amount of time. In some embodiments the memory device can store the information for a period of ten days before it is erased.

In preferred embodiments an external device communicates with the communication assembly within the reader's assembly. An external device can wirelessly communicate with a reader assembly, but can also communicate with a third party, including without limitation a patient, medical personnel, clinicians, laboratory personnel, or others in the health care industry.

In some embodiments the external device can be a computer system, server, or other electronic device capable of storing information or processing information. In some embodiments the external device includes one or more computer systems, servers, or other electronic devices capable of storing information or processing information. In some embodiments an external device may include a database of subject information, for example but not limited to, medical records or subject history, clinical trial records, or preclinical trial records. In preferred embodiments, an external device stores protocols to be run on a fluidic device which can be transmitted to the communication assembly of a reader assembly when it has received an identifier indicating which fluidic device has been inserted in the reader assembly. In some embodiments a protocol can be dependent on a fluidic device identifier. In some embodiments the external device stores more than one protocol for each fluidic device. In other embodiments subject information on the external device includes more than one protocol. In preferred embodiments the external server stores mathematical algorithms to process a photon count sent from a communication assembly and in some embodiments to calculate the analyte concentration in a bodily fluid sample.

In some embodiments the external device can include one or more servers as are known in the art and commercially available. Such servers can provide load balancing, task management, and backup capacity in the event of failure of one or more of the servers or other components of the external device, to improve the availability of the server. A server can also be implemented on a distributed network of storage and processor units, as known in the art, wherein the data processing according to the present invention reside on workstations such as computers, thereby eliminating the need for a server.

A server can includes a database and system processes. A database can reside within the server, or it can reside on another server system that is accessible to the server. As the information in a database may contains sensitive information, a security system can be implemented that prevents unauthorized users from gaining access to the database.

One advantage of the present invention is that information can be transmitted from the external device back to not only the reader assembly, but to other parties or other external devices, for example without limitation, a PDA or cell phone. Such communication can be accomplished via a wireless network as disclosed herein. In some embodiments a calculated analyte concentration or other subject information can be sent to, for example but not limited to, medical personal or the subject.

Methods of Use

The subject apparatus and systems provide an effective means for real-time detection of analytes indicative of an influenza viral infection present in a bodily fluid from a subject.

One aspect of the present invention is a method of detecting an analyte indicative of an influenza viral infection in a sample of bodily fluid. The analyte may be indicative of an influenza type A, type B, or type C viral infection. The analyte may comprise at least one surface glycoprotein of an influenza virus. Exemplary surface glycoproteins are, without limitation, a hemagglutinin and a neuraminidase. Hemagglutinin surface proteins include H1, H2, H3, H4, H5, H6, H7, H8, H9, H10, H11, H12, H13, H14, H15, and H16.

Neuraminidase surface proteins include N1, N2, N3, N4, and N5. The analyte may also comprise an antibody to a surface glycoprotein of an influenza virus.

One aspect of the present invention is a method for detecting a plurality of analytes, at least two of which are indicative of an influenza viral infection in a sample of bodily fluid. The analytes may be indicative of an influenza type A, type B, or type C viral infection. The analytes may comprise a plurality of surface glycoproteins of an influenza virus. In some embodiments the plurality of surface glycoproteins comprises a hemagglutinin and a neuraminidase. The hemagglutinin may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5. In preferred embodiments the method detects for both hemagglutinin H5 and neuraminidase N1. In one embodiment the method provides for detection of H5 and N1 in the same viral particle(s) (see FIG. 15).

One further aspect of the present invention is a method for detecting a plurality of analytes incorporated into a single entity such as a viral particle or cell or cell fragment. In this aspect the plurality of analytes are preferably a combination or complex of analytes, at least two of which are indicative of an influenza viral infection in a sample of bodily fluid. The analytes may be indicative of an influenza type A, type B, or type C viral infection. The plurality of analytes may comprise a combination or complex of surface glycoproteins of an influenza virus. In some embodiments the plurality of analytes may be a combination of surface glycoproteins comprising a combination of a hemagglutinin and a neuraminidase. The hemagglutinin may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5. In preferred embodiments the combination of analytes is associated with a virulent strain of influenza such as the H5N1 combination. This aspect of the invention is specific for detecting the combination of the plurality of analytes. It can distinguish between infection with a virulent strain such as a combination of $H_5N_1$ and a putative-infection with a different combination of analytes.

In some embodiments the method detects a plurality of human antibodies to viral antigens such as antibodies to surface glycoproteins of an influenza virus.

In some embodiments the analyte of interest may be a complex of an analyte indicative of an influenza viral infection in a sample of bodily fluid and a human antibody to the analyte. The analyte may be any analyte indicative of an influenza viral infection described herein, but is preferably the H5 hemagglutinin, the N1 neuraminidase, or the H5N1 complex of the H5 and N1 surface glycoproteins.

A further aspect of the present invention is a method for detecting a plurality of analytes, wherein at least one analyte is indicative of an influenza viral infection in a sample of bodily fluid, and wherein at least one analyte is a biomarker in the sample of bodily fluid indicative of the stress imposed on the human body by the viral infection or an indicator of the body's response to the infection. The at least one analyte indicative of an influenza viral infection may be any analyte indicative of an influenza viral infection described herein. Exemplary biomarkers indicative of the stress imposed on the human body by the viral infection include, without limitation, CRP, TNF$\alpha$, interleukins and the like. Exemplary biomarkers indicative of the body's defensive reaction to the virus include antibodies to the virus, particularly of the IgM isotype.

The subject apparatus and systems have a spectrum of utility in, for example, disease diagnosis and disease detection.

Accordingly, in one embodiment, the present invention provides a method of detecting an analyte indicative of an influenza viral infection in a bodily fluid from a subject comprises providing a fluidic device comprising at least one sample collection unit, an immunoassay assembly containing immunoassay reagents, a plurality of channels in fluid communication with said sample collection unit and/or said immunoassay assembly; actuating said fluidic device and directing said immunoassay reagents within said fluidic device; allowing a sample of bodily fluid suspected to contain said analyte to react with said immunoassay reagents contained within said assay immunoassay assembly to yield a detectable signal indicative of the presence of said analyte in said bodily fluid; and detecting said detectable signal generated from said analyte initially collected in said sample of bodily fluid. Preferably, a sample of bodily fluid of less than about 500 ul is used for one or more of these applications.

As used herein, the term "subject" and "patient" is used interchangeably, which refers to an animal, preferably an avian (bird) or a mammalian species (for example, human). The term avian as used herein includes poultry. Mammals include, but are not limited to, murines, simians, humans, farm animals, sport animals, and pets.

As used herein, in some aspects the terms "reagents" and "reactants" are used interchangeably.

In some embodiments a sample of bodily fluid can first be provided to the fluidic device by any of the methods described herein. The fluidic device can then be inserted into the reader assembly. An identification detector housed within the reader assembly can detect an identifier of the fluidic device and communicate the identifier to a communication assembly, which is preferably housed within the reader assembly. The communication assembly then transmits the identifier to an external device which transmits a protocol to run on the fluidic device based on the identifier to the communication assembly. A controller preferably housed within the reader assembly controls actuating elements including at least one pump and one valve which interact with the fluidic device to control and direct fluid movement within the device. In some embodiments the first step of the assay is a wash cycle where all the surfaces within the fluidic device are wetted using a wash buffer. The fluidic device is then calibrated using a calibration assembly by running the same reagents as will be used in the assay through the calibration reaction sites, and then a luminescence signal from the reactions sites is detected by the detection means, and the signal is used in calibrating the fluidic device. The sample containing the analyte is introduced into the fluidic channel. The sample may be diluted and further separated into plasma or other desired component at a filter. The separated sample now flows through the reaction sites and analytes present therein will bind to reactants bound thereon. The plasma of sample fluid is then flushed out of the reaction wells into a waste chamber. Depending on the assay being run, appropriate reagents are directed through the reaction sites to carry out the assay. All the wash buffers and other reagents used in the various steps, including the calibration step, are collected in wash tanks. The signal produced in the reaction sites is then detected by any of the methods described herein.

A variety of assays may be performed on a fluidic device according to the present invention to detect an analyte of interest in a sample. A wide diversity of labels is available in the art that can be employed for conducting the subject assays. In some embodiments labels are detectable by spectroscopic, photochemical, biochemical, immunochemical, or chemical means. For example, useful nucleic acid labels include 32P, 35S, fluorescent dyes, electron-dense reagents, enzymes, biotin, digoxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include radionucleides, enzymes, substrates, cofactors, inhibitors, fluorescent moieties, chemiluminescent moieties, bioluminescent labels, calorimetric labels, or magnetic particles. Labeling agents optionally include, for example, monoclonal antibodies, polyclonal antibodies, proteins, or other polymers such as affinity matrices, carbohydrates or lipids. Detection proceeds by any of a variety of known methods, including spectrophotometric or optical tracking of radioactive or fluorescent markers, or other methods which track a molecule based upon size, charge or affinity A detectable moiety can be of any material having a detectable physical or chemical property. Such detectable labels have been well-developed in the field of gel electrophoresis, column chromatograpy, solid substrates, spectroscopic techniques, and the like, and in general, labels useful in such methods can be applied to the present invention. Thus, a label includes without limitation any composition detectable by spectroscopic, photochemical, biochemical, immunochemical, electrical, optical, thermal or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non-radioactive labels are often attached by indirect means. Generally, a ligand molecule is covalently bound to a polymer. The ligand then binds to an anti-ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol and dioxetanes Methods of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (e.g., light) when they move from an "excited state" to a lower energy state (usually the ground state). There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6, 7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include N-alkyl acridinum esters and dioxetanes. Alternatively, luciferins may be used in conjunction with luciferase or lucigenins to provide bioluminescence.

In some embodiments immunoassays are run on the fluidic device. While competitive binding assays, which are well known in the art, may be run in some embodiments, in certain embodiments a two-step method is used which eliminates the need to mix a conjugate and a sample before exposing the mixture to an antibody, which may be desirable when very small volumes of sample and conjugate are used, as in the fluidic device of the present invention. A two-step assay has additional advantages over the competitive binding assays when used with a fluidic device as described herein. It combines the ease of use and high sensitivity of a sandwich (competitive binding) immunoassay with the ability to assay small molecules.

Figure 10:
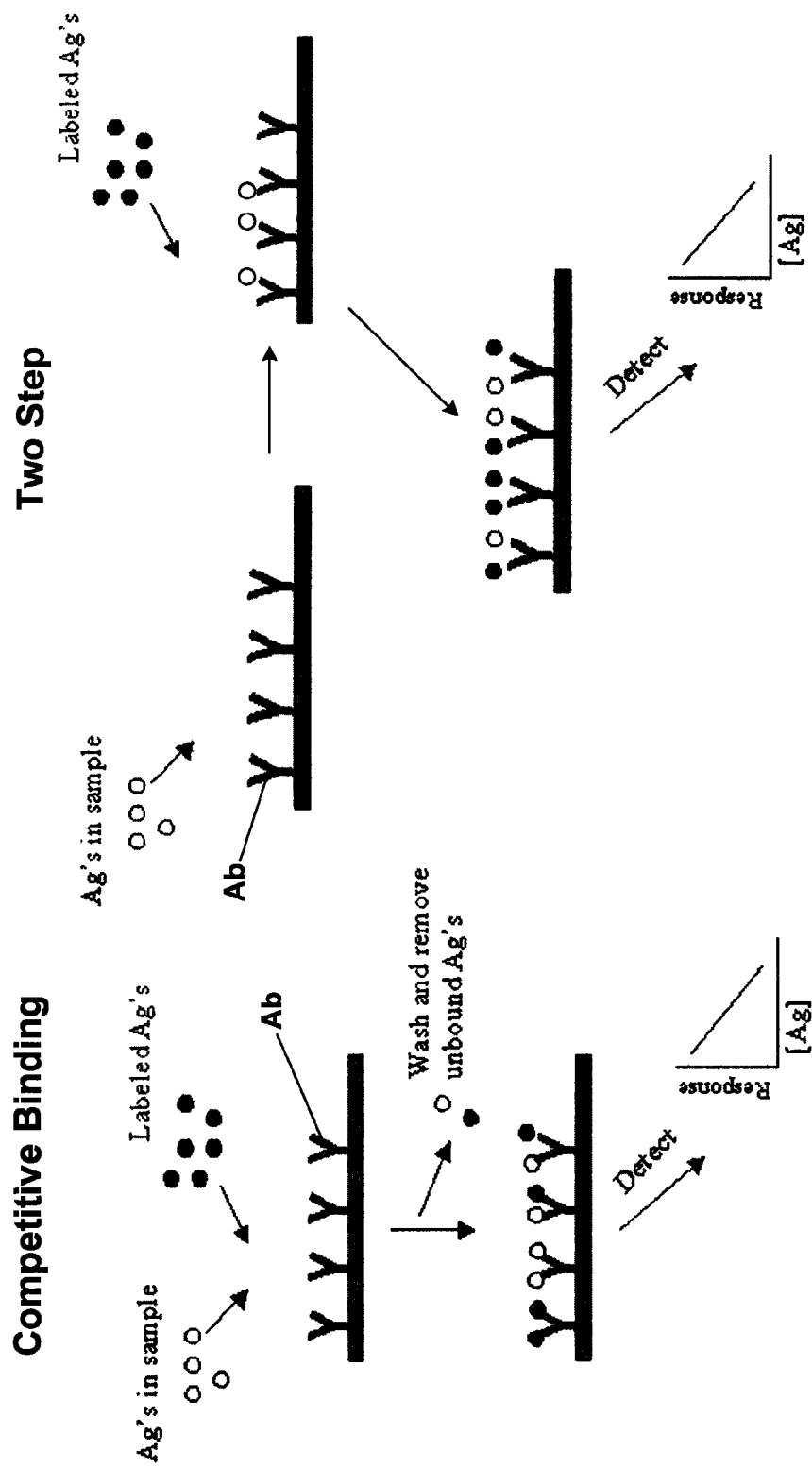
FIG. 10 compares a two-step assay with a competitive binding assay.

In an exemplary two-step assay shown in FIG. 10, the sample containing analyte ("Ag") first flows over a reaction site containing antibodies ("Ab"). The antibodies bind the analyte present in the sample. After the sample passes over the surface, a solution with analyte conjugated to a marker ("labeled Ag") at a high concentration is passed over the surface. The conjugate saturates any of the antibodies that have not yet bound the analyte. Before equilibrium is reached and any displacement of pre-bound unlabelled analyte occurs, the high-concentration conjugate solution is washed off. The amount of conjugate bound to the surface is then measured by the appropriate technique, and the detected conjugate is inversely proportional to the amount of analyte present in the sample.

Figure 11:
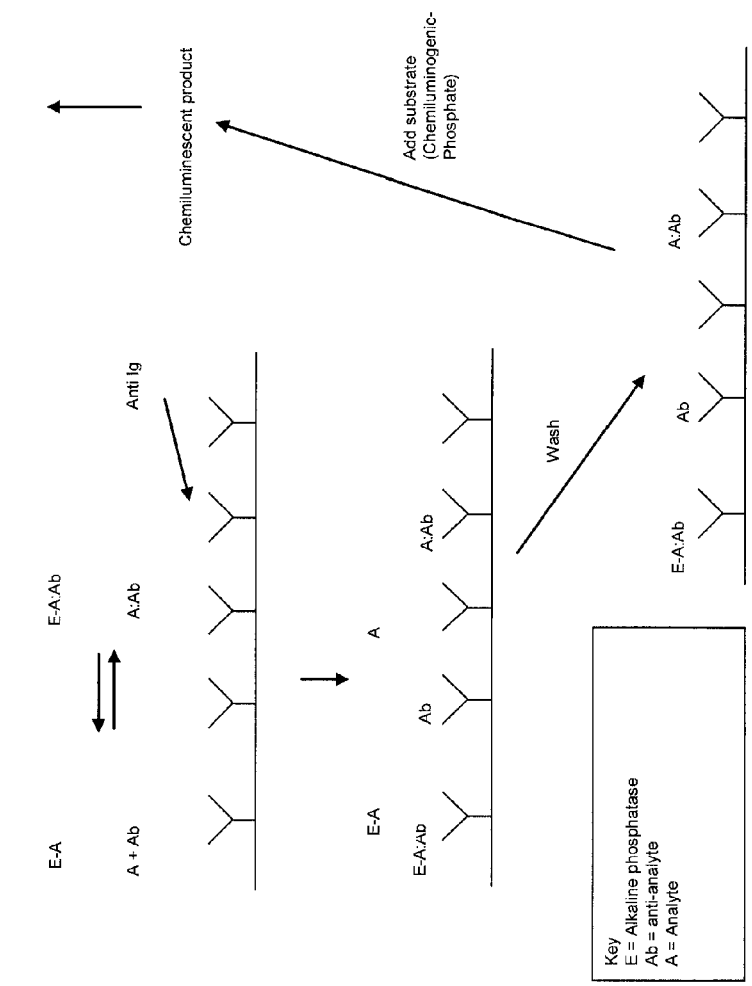
FIG. 11 shows an exemplary two-step chemiluminescence enzyme immunoassay.
Figure 12:
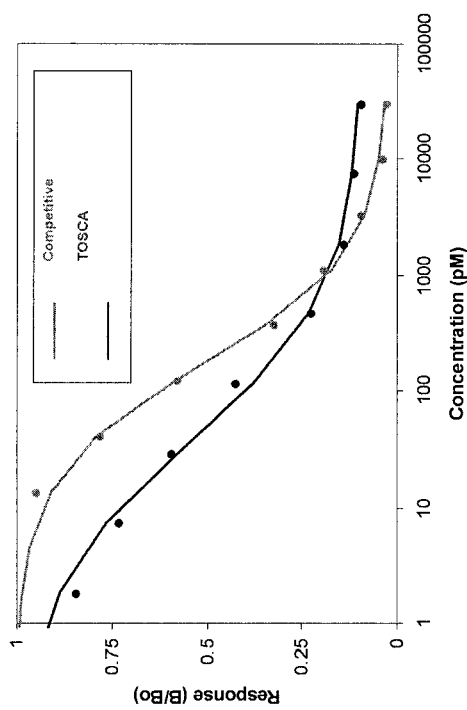
FIG. 12 shows the increased sensitivity of the two-step chemiluminescence enzyme immunoassay.

An exemplary measuring technique for a two-step assay is a chemiluminescence enzyme immunoassay as shown in FIG. 11. As is known in the field, the marker can be a commercially available marker such as dioxitane-phosphate, which is not luminescent but becomes luminescent after hydrolysis by, for example, alkaline phosphatase. An enzyme such as alkaline phosphatase is also passed over the substrate to cause the marker to luminesce. In some embodiments the substrate solution is supplemented with enhancing agents such as, without limitation, fluorescein in mixed micelles, soluble polymers, or PVC which create a much brighter signal than the luminophore alone. Moreover, an alkaline phosphatase conjugate with a higher turnover number than that used in the commercial assay is employed. This allows signal generation to proceed much more rapidly and a higher overall signal is achieved. The increased sensitivity of the two-step chemiluminescent enzyme immunoassay (TOSCA) is illustrated in FIG. 12. FIG. 12 shows that for analytes in the picomolar concentration, TOSCA is able to provide a more robust signal (higher sensitivity) than a competitive binding assay. Use of a two-step binding assay thus contributes to higher sensitivity capabilities of the present invention.

Figure 13:
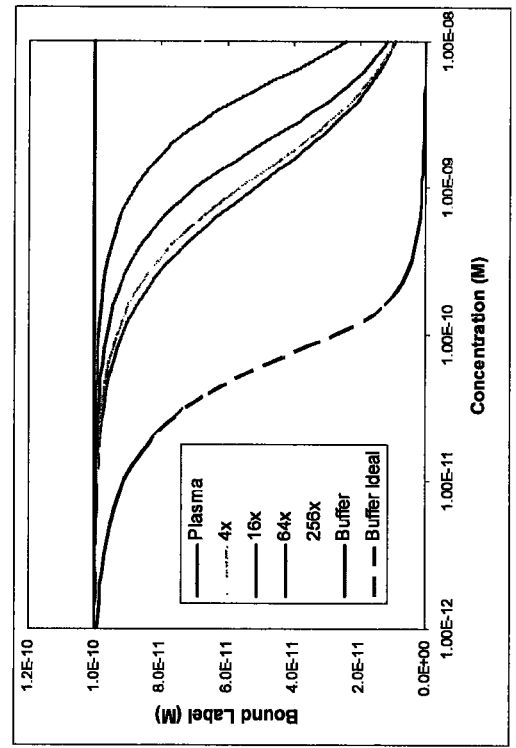
FIG. 13 shows the ability of TOSCA to assay less than ideal samples and maintain desired sensitivity.
Figure 13:
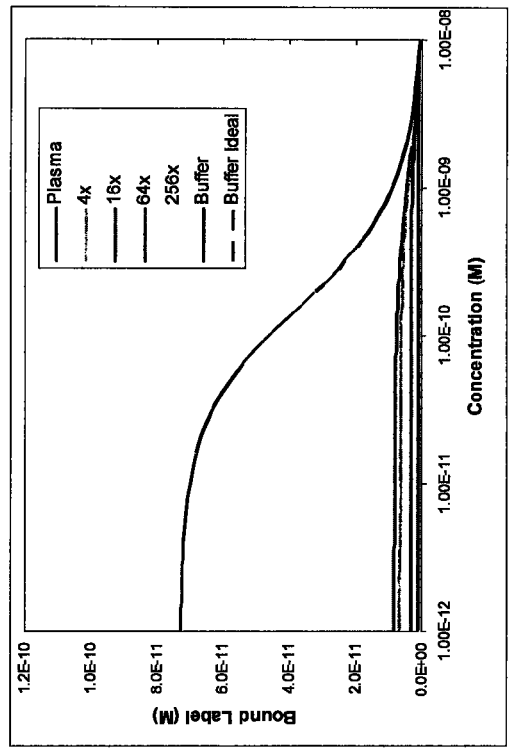

Additionally, TOSCA is less sensitive to matrix effects than other methodologies. This allows one to work with samples that have not been extensively pre-processed using standard laboratory techniques such as, for example, solid phase extraction and chromatography. The ability of TOSCA to assay less than ideal samples and maintain desired sensitivity is illustrated in FIG. 13. Compared to competitive binding assay, for all sample preparations (and dilutions), TOSCA has better sensitivity than competitive binding.

One useful immunoassay that can be run on the fluidic device is ELISA (Enzyme-Linked ImmunoSorbent Assay). Performing an ELISA generally involves at least one antibody capable of binding an antigen of interest (i.e., an analyte that is indicative of influenza viral infection). A sample containing or suspected to contain the antigen of interest is immobilized on a support (e.g., a microtiter plate, a well or other support having a surface for immobilization) either non-specifically (e.g., via adsorption to the surface) or specifically (e.g., via capture by another antibody specific to the same antigen, in a "sandwich" ELISA). After the antigen is immobilized the detection antibody is added, forming a complex with the antigen. The detection antibody can be conjugated to an enzyme, or can itself be detected by a secondary antibody which is in turn conjugated to an enzyme. Upon addition of a substrate for the conjugated enzyme, a detectable signal is generated which indicates the presence and/or quantity of the antigen in the sample. The choice of substrates will depend on the enzyme conjugated. Suitable substrates include fluorogenic and chromogenic substrates. One of skill in the art would be knowledgeable as to the parameters that can be modified to increase the signal detected as well as other variations of ELISAs known in the art.

Figure 14:
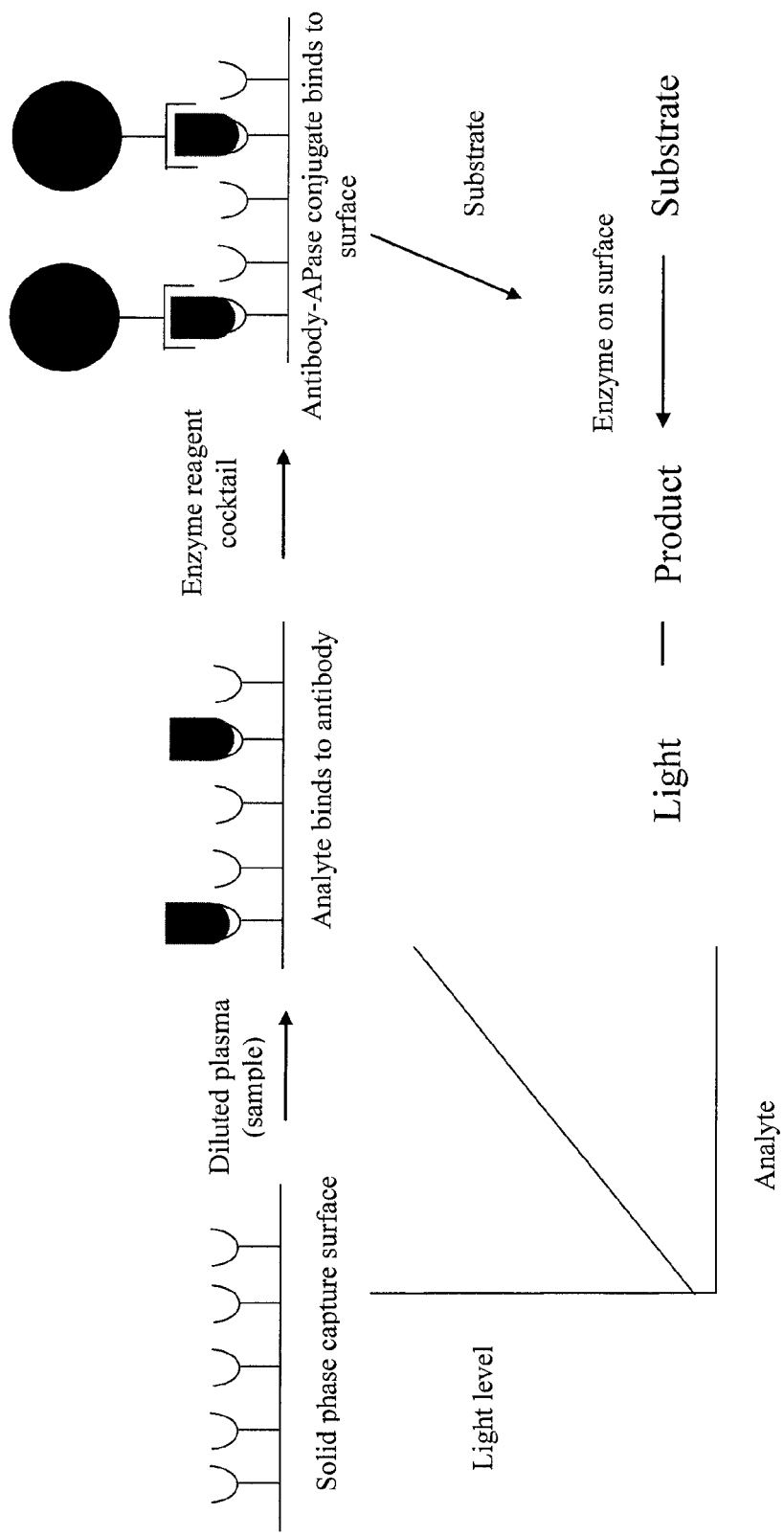
FIG. 14 shows an exemplary ELISA.

FIG. 14 illustrates a typical ELISA. As shown, a solid phase capture surface can include an attached first antibody to which diluted plasma (sample) can be added. Analyte if present in the sample can bind to the first antibody and become immobilized. An enzyme reagent can be added that includes, for example, an antibody coupled or conjugated to an enzyme (e.g., alkaline phosphatase). If the antibody portion of the enzyme reagent can bind the analyte, then the enzyme reagent also becomes immobilized at the capture surface. Addition of a substrate for the enzyme can result in a product producing an effect, for example, light that can be measured and plotted as shown. In this manner the amount of analyte present in a sample can be measured.

Figure 15:
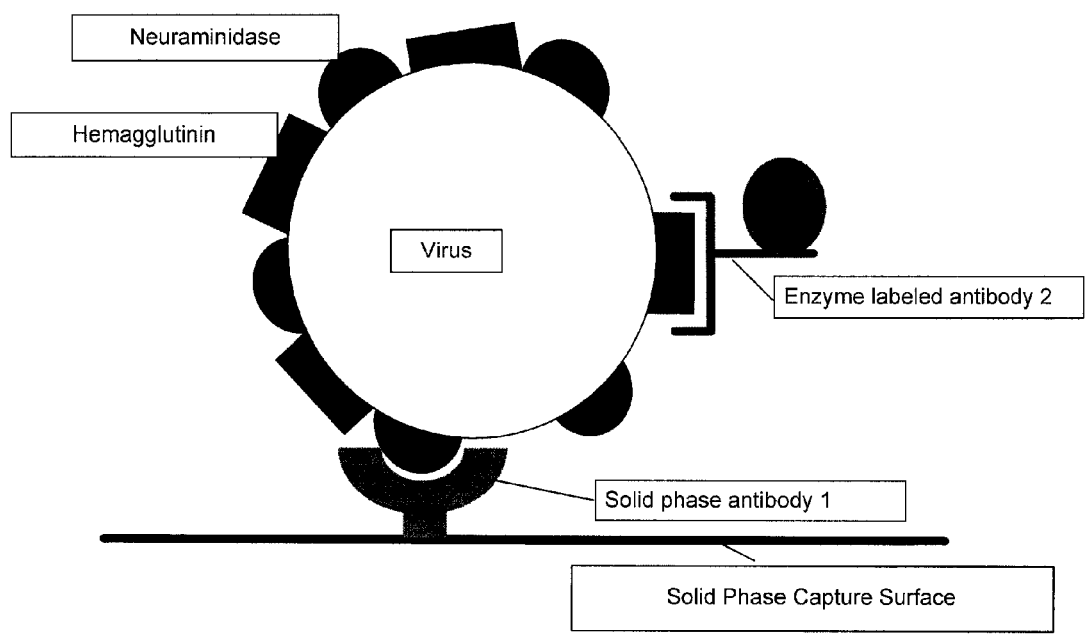
FIG. 15 shows an exemplary ELISA for a virus.

FIG. 15 illustrates an exemplary ELISA for use with the fluidic device of the invention. As shown, a solid phase capture surface of the device can include a first antibody, "solid phase antibody 1", that is surface immobilized and specific for a test antigen (e.g., antibody specific for a neuraminidase on a virus). If the test antigen is present in a test sample (e.g., blood) exposed to the solid phase antibody 1 then the test antigen can become immobilized (captured) at the capture surface. Subsequently provided is a second antibody that is specific for a second test antigen and includes a conjugated detectable compound, shown as "enzyme labeled antibody 2" (e.g., enzyme labeled antibody specific for a hemagglutinin on a virus), that can be added after the test sample (e.g., blood). Binding and subsequent detection of the second conjugated antibody at the capture surface can indicate the presence of the first and second test antigens in the test sample. In use, the first and second test antigens can include any of the neuraminidase or hemagglutinin types described herein.

Although different first and second antigens (and antibodies) are used in the illustrated example, it is envisioned that a single type of test antigen could be detected using two forms of the same antibody (i.e., an immobilized solid phase form for antigen capture and an enzyme labeled form for detection).

The term "analytes" according to the present invention includes without limitation drugs, prodrugs, pharmaceutical agents, drug metabolites, biomarkers such as expressed proteins and cell markers, antibodies, antigens, viruses, serum proteins, cholesterol, polysaccharides, nucleic acids, biological analytes, biomarker, gene, protein, or hormone, or any combination thereof. At a molecular level, the analytes can be polypeptide glycoprotein, polysaccharide, lipid, nucleic acid, and a combination thereof.

Of interest are biomarkers are associated with a particular disease or with a specific disease stage. Such analytes include but are not limited to those associated with autoimmune diseases.

Also of interest are analytes that are indicative of a microorganism. Exemplary microorganisms include but are not limited to bacterium, virus, fungus and protozoa.

The analyte may be indicative of an influenza type A, type B, or type C viral infection. The analyte may comprise at least one surface glycoprotein of an influenza virus. Exemplary surface glycoproteins are, without limitation, a hemagglutinin and a neuraminidase. Hemagglutinin surface proteins include H1, H2, H3, H4, H5, H6, H7, H8, H9, H10, H11, H12, H13, H14, H15, and H16. Neuraminidase surface proteins include N1, N2, N3, N4, and N5.

One aspect of the present invention is a system for detecting a plurality of analytes, at least two of which are indicative of an influenza viral infection in a sample of bodily fluid. The analytes may be indicative of an influenza type A, type B, or type C viral infection. The analytes may comprise a plurality of surface glycoproteins of an influenza virus. In some embodiments the plurality of surface glycoproteins comprises a hemagglutinin and a neuraminidase. The hemagglutinin may be selected from the group consisting of H1, H2, H3, H4, H5, H6, H7, H8, H9, H10, H11, H12, H13, H14, H15, and H16, and the neuraminidase may be selected from the group consisting of N1, N2, N3, N4, and N5. In preferred embodiments the hemagglutinin is H5 and the neuraminidase is N1. The system is capable of detecting and/or quantifying the analytes of particular interest.

By detecting the presence of the viral antigens or antibodies to the antigens, for example, the fluidic device can detect the presence of a type of influenza virus in the sample of bodily fluid from the subject.

Analytes that can be detected by the subject method also include blood-born pathogens selected from a non-limiting group that consists of *Staphylococcus epidermidis, Escherichia coli,* methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans.*

Analytes that can be detected by the subject method also encompass a variety of sexually transmitted diseases selected from the following: gonorrhea (*Neisseria gorrhoeae*), syphilis (*Treponena pallidum*), Chlamydia (*Chlamydia trachomatis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

It is envisioned that in some embodiments the present invention provides for monitoring an infection by a pathogen either directly through detection of the pathogen or indirectly, for example, by detection of a analyte associated with a pathogen (e.g., a viral antigen) or even by detection of an antibody to a component or product associated with a pathogen (e.g., an antibody to a viral antigen). It is also envisioned that a pathogen can be indirectly detected through an immune-related response to the pathogen. Detection of the pathogen can be performed on a test sample from a subject that is asymptomatic or symptomatic for the pathogen. Detection of the pathogen can be performed on a test sample from a subject before, during or after infection with the pathogen. As such, it is envisioned that an early stage infection (e.g., in some cases an asymptomatic infection), or any later phase of infection can be monitored for the pathogen of interest.

A wide range of pathogen concentrations in a sample from a subject can be detected either directly or indirectly as discussed above using the invention. The amount of pathogen present in a test sample can be expressed in any of a number of ways well known in the art. By way of non-limiting examples, the number of pathogens can be expressed as viral burden (e.g., where the infection is a viral infection), infectious units (IU), and/or infectious units per million cells or milliliter (IUPM). In one example, it is envisioned that pathogens can be detected in a test sample at a concentration of from 100 IU per ml of sample up to $1 \times 10^9$ IU per ml of sample using the invention. In another example pathogens can be detected from 100 IU per ml of sample up to 1000 IU per ml of sample using the invention. In yet another example pathogens can be detected from 1,000 IU per ml of sample up to $1 \times 10^6$ IU per ml of sample using the invention.

In a separate embodiment, the present invention provides a method of monitoring more than one pharmacological parameter useful for assessing efficacy and/or toxicity of an anti-influenza therapeutic agent. The method comprises subjecting a sample of bodily fluid from a subject administered with the anti-influenza therapeutic agent to a fluidic device for monitoring said more than one pharmacological parameter, said fluidic device comprising at least one sample collection unit, and an assay assembly comprising reaction reagents; actuating said fluidic device and directing said immunoassay reagents within said fluidic device; allowing said sample of bodily fluid to react with immunoassay reagents to yield detectable signals indicative of the values of the more than one pharmacological parameter from said sample; and detecting said detectable signal generated from said sample of bodily fluid. Where desired, the method further involves repeating the steps at a time interval prompted by a wireless signal communicated to the subject.

For the purposes of this invention, a "therapeutic agent" is intended to include any substances that have therapeutic utility and/or potential. Such substances include but are not limited to biological or chemical compounds such as a simple or complex organic or inorganic molecules, peptides, proteins (e.g. antibodies) or a polynucleotides (e.g. anti-sense). A vast array of compounds can be synthesized, for example polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the subject. Similarly, if any of the pharmacodynamic (PD) parameters fall outside the desired range during a treatment regime, immediate action may have to be taken as well.

In preferred embodiments physical parameter data is stored in or compared to store profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more subjects to enter clinical trials in a safe fashion earlier than currently allowed. In another embodiment biomarkers discovered in human tissue studies can be targeted by the device for improved accuracy in determining drug pathways and efficacy in cancer studies.

In another embodiment, the present invention provides a method of detecting at least two distinct analytes indicative of an influenza viral infection of different concentrations in a bodily fluid from a subject comprises providing a fluidic device comprising a sample collection unit, an assay assembly, and a plurality of channels in fluid communication with said sample collection unit and/or said assay assembly; allowing a sample of bodily fluid to react with a plurality of reactants contained in said assay assembly to yield signals indicative of the concentrations of said at least two analytes; and detecting said signals that are indicative of the presence or absence of the at least two distinct analytes, wherein said signals are detectable over a range of 3 orders of magnitude.

Currently, a need exists for the detecting more than one analyte indicative of an influenza viral infection where the analytes are present in widely varying concentration range, for example, one analyte is in the pg/ml concentration and another is in the ng/ml concentration Chemiluminescence-ELISA has the ability to simultaneously assay analytes that are present in the same sample in a wide concentration range. Another advantage for being able to detect concentrations of different analytes present in a wide concentration range is the ability to relate the ratios of the concentration of these analytes to safety and efficacy of multiple drugs administered to a subject. For example, unexpected drug-drug interactions can be a common cause of adverse drug reactions. A real-time, concurrent measurement technique for measuring different analytes would help avoid the potentially disastrous consequence of adverse drug-drug interactions.

Being able to monitoring the rate of change of an analyte concentration or PD or PK over a period of time in a single subject, or performing trend analysis on the concentration, PD, or PK, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

Accordingly, the present invention provides a method of performing a trend analysis on the concentration of an analyte indicative of an influenza viral infection in a subject. The method comprise a) providing a fluidic device comprising at least one sample collection unit, an immunoassay assembly containing immunoassay reagents, a plurality of channels in fluid communication with said sample collection unit and/or said immunoassay assembly; b) actuating said fluidic device and directing said immunoassay reagents within said fluidic device; c) allowing a sample of bodily fluid to react with said immunoassay reagents contained within said assay immunoassay assembly to yield a detectable signal indicative of the presence of said analyte in said sample; d) detecting said detectable signal generated from said analyte collected in said sample of bodily fluid; and e) repeating steps a) through d) for a single subject over a period of time to detect concentrations of said analyte, thereby performing said trend analysis.

In some embodiments, a method of detecting an analyte indicative of an influenza viral infection in a bodily fluid from a subject using an assay transmitted from an external device is provided. The method comprises providing a fluidic device comprising at least one sample collection unit and an immunoassay assembly containing immunoassay reagents; detecting said fluidic device and wirelessly transmitting an immunoassay protocol to said device; allowing a sample of bodily fluid to react with immunoassay reagents to yield a detectable signal indicative of the presence of said analyte using said transmitted immunoassay protocol; and detecting said detectable signal.

Communication between a reader assembly and an external storage device allows for a reader assembly of the present invention to download a fluidic device-specific protocol to run on the fluidic device based on the identity of the fluidic device. This allows a reader assembly to be used interchangeably with any appropriate fluidic device described herein. In addition, the external device can store a plurality of protocols associated with a given fluidic device, and depending on, for example, a subject's treatment regime or plan, different protocols can be communicated from the external device to the reader assembly to be run on the fluidic device to detect a variety of analytes indicative of an influenza viral infection. The external device can also store a plurality of protocols associated not only with a fluidic device, but also with a particular subject or subjects, such that a protocol can be associated with a subject as well as with a fluidic device.

The present invention allows for automatic quantification of a pharmacological parameter of a subject as well as automatic comparison of the parameter with, for example, the subject's medical records which may include a history of the monitored parameter, or medical records of another group of subjects. Coupling real-time analyte monitoring with an external device which can store data as well as perform any type of data processing or algorithm, for example, provides a device that can assist with typical subject care which can include, for example, comparing current subject data with past subject data. The present invention therefore creates a business method which effectively performs at least part of the monitoring of a subject that is currently performed by medical personnel.

One of the significant advantages of the envisioned network is illustrated in FIG. 20. As all the information is securely channeled through the internet, this allows the simultaneous sharing of the information with various interested parties, while satisfying the appropriate clinical, regulatory and business needs.

In some embodiments, the present invention provides a method of transmitting a pharmacological parameter of a subject via a handheld device comprises providing a fluidic device comprising at least one sample collection unit and an assay assembly; allowing a sample of bodily fluid to react with reactants contained within said assay assembly to yield a detectable signal indicative of the presence of said analyte indicative of an influenza virus; detecting said detectable signal; transmitting said signal to an external device; processing said signal in said external device; and transmitting said processed signal via a handheld device.

One advantage of the current invention is that assay results can be substantially immediately communicated to any third party that may benefit from obtaining the results. For example, once the analyte concentration is determined at the external device, it can be transmitted to a patient or medical personnel who may need to take further action. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

In some embodiments a method of automatically selecting a protocol to be run on a fluidic device comprises providing a fluidic device comprising an identifier detector and an identifier; detecting said identifier with said identifier detector; transferring said identifier to an external device; and selecting a protocol to be run on said fluidic device from a plurality of protocols on said external device associated with said identifier.

By detecting each fluidic device based on an identifier associated with the fluidic device after it is inserted in the reader assembly, the system of the present invention allows for fluidic device-specific protocols to be downloaded from an external device and run on the fluidic device. In some embodiments the external device can store a plurality of protocols associated with the fluidic device or associated with a particular subject or group of subjects. For example, when the identifier is transmitted to the external device, software on the external device can obtain the identifier. Once obtained, software on the external device, such as a database, can use the identifier to identify protocols stored in the database associated with the identifier. If only one protocol is associated with the identifier, for example, the database can select the protocol and software on the external device can then transmit the protocol to the communication assembly on the reader assembly. The ability to use protocols specifically associated with a fluidic device allows for any appropriate fluidic device to be used with a single reader assembly, and thus virtually any analyte of interest can be detected with a single reader assembly.

In some embodiments multiple protocols may be associated with a single identifier. For example, if it is beneficial to detect from the same subject an analyte once a week, and another analyte twice a week, protocols on the external device associated with the identifier can also each be associated with a different day of the week, so that when the identifier is detected, the software on the external device can select a specific protocol that is associated with the day of the week.

In some embodiments a subject may be provided with a plurality of fluidic devices to use to detect a variety of analytes. A subject may, for example, use different fluidic devices on different days of the week. In some embodiments the software on the external device associating the identifier with a protocol may include a process to compare the current day with the day the fluidic device is to be used based on a clinical trial for example. If for example, the two days of the week are not identical, the external device can wirelessly send notification to the subject using any of the methods described herein or known in the art to notify them that an incorrect fluidic device is in the reader assembly and also of the correct fluidic device to use that day. This example is only illustrative and can easily be extended to, for example, notifying a subject that a fluidic device is not being used at the correct time of day.

In some embodiments, the present invention provides a method of obtaining pharmacological data useful for assessing efficacy and/or toxicity of an anti-influenza pharmaceutical agent from a test animal. The method involves the steps of a) providing a fluidic device comprising at least one sample collection unit, an assay assembly; and a plurality of channels in fluid communication with said sample collection unit and/ or said assay assembly; b) allowing a sample of biological fluid of less than about 50 ul to react with reactants contained within said assay assembly to yield a detectable signal generated from an analyte indicative of an influenza viral infection initially collected in said sample that is indicative of a pharmacological parameter; and c) detecting said detectable signal; and d) repeating the reaction and detection steps with a second sample of biological fluid from the same test animal. In a related embodiment, the present invention provides a method comprising a) providing a fluidic device comprising at least one sample collection unit, an assay assembly; and a plurality of channels in fluid communication with said sample collection unit and/or said assay assembly; b) allowing a sample of biological fluid to react with reactants contained within said assay assembly to yield a detectable signal generated from an analyte initially collected in said sample that is indicative of a pharmacological parameter; and c) detecting said detectable signal; and d) repeating the reaction and detection steps with a second sample of biological fluid from the same test animal, wherein the animal is not subjected to anesthesia.

When using laboratory animals in preclinical testing of an anti-influenza pharmaceutical agent, it is often necessary to kill the test subject to extract enough blood to perform an assay to detect an analyte of interest. This has both financial and ethical implications, and as such it may be advantageous to be able to draw an amount of blood from a test animal such that the animal does not need to be killed. In addition, this can also allow the same test animal to be tested with multiple pharmaceutical agents at different times, thus allowing for a more effective preclinical trial. On average, the total blood volume in a mouse, for example, is 6-8 mL of blood per 100 gram of body weight. A benefit of the current invention is that only a very small volume of blood is required to perform preclinical trials on mice or other small laboratory animals. In some embodiment between about 1 microliter and about 50 microliters are drawn. In preferred embodiment between about 1 microliter and 10 microliters are drawn. In preferred embodiments about 5 microliters of blood are drawn.

A further advantage of keeping the test animal alive is evident in a preclinical time course study. When multiple mice, for example, are used to monitor the levels of an analyte in a test subject's bodily fluid over time, the added variable of using multiple subjects is introduced into the trial. When, however, a single test animal can be used as its own control over a course of time, a more accurate and beneficial preclinical trial can be performed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system comprising:
   a) a fluidic device, said fluidic device comprising a sample collection unit and a cartridge, wherein said cartridge comprises an immunoassay assembly and an identifier, wherein said sample collection unit allows a sample of bodily fluid from a subject suspected to contain an influenza viral particle to react with a first immunoassay reagent and a second immunoassay reagent, both of which being contained within said immunoassay assembly, wherein said first immunoassay reagent binds to a hemagglutinin molecule to form a first immune complex on said influenza viral particle, and wherein said second immunoassay reagent binds to a neuraminidase molecule to form a second immune complex on said influenza viral particle, said immune complexes yield one or more detectable signals indicative of the simultaneous presence of hemagglutinin and neuraminidase on said influenza viral particle, wherein either the first or second immunoassay reagent is immobilized on a solid support, and wherein said simultaneous presence of hemagglutinin and neuraminidase is indicative of the presence of said influenza viral particle;

b) a reader assembly comprising a detection assembly for detecting said one or more detectable signals; and c) a communication assembly for transmitting said detected signal to an external device, and wherein said external device is configured to transmit a protocol in response to said identifier on said cartridge, and wherein said protocol in turn effects a reaction in said immunoassay assembly to generate said detectable signal.

2. The system of claim 1, wherein detection of said hemagglutinin and neuraminidase is indicative of an influenza type A viral infection.

3. The system of claim 1, wherein detection of said hemagglutinin and neuraminidase is indicative of an influenza type B viral infection.

4. The system of claim 1, wherein said hemagglutinin is selected from the group consisting of H1, H2, H3, H4, H5, H6, H7, H8, H9, H10, H11, H12, H13, H14, H15, and H16, and said neuraminidase is selected from the group consisting of N1, N2, N3, N4, and N5.

5. The system of claim 1, wherein said hemagglutinin is H5 and said neuraminidase is N1.

6. The system of claim 1, wherein said subject is a human.

7. The system of claim 1, wherein said subject is an animal.

8. The system of claim 7, wherein said animal is poultry.

9. A fluidic device comprising:

a cartridge comprising a plurality of immunoassay reactants, at least two of which bind different analytes present on an influenza viral particle in a bodily fluid from a subject, wherein at least one member of said different analytes is a hemagglutinin selected from H1, H2, H3, H4, H5, H6, H7, H8, H9, H10, H11, H12, H13, H14, H15, and H16, and at least one other member of said different analytes is a neuraminidase selected from N1, N2, N3, N4 and N5, and wherein said cartridge is adapted to allow said bodily fluid to react with said plurality of reactants to yield one or more detectable signals that are indicative of the presence of hemagglutinin and neuraminidase simultaneously present on an influenza viral particle in said bodily fluid.

10. The fluidic device of claim 9, where said cartridge further comprises a sample collection unit and an assay assembly that comprises said reactants.

11. The fluidic device of claim 10, where said assay assembly comprises an immunoassay assembly.

12. The fluidic device of claim 9, wherein said cartridge comprises an identifier, wherein said identifier is configured to be read by an identifier detector that reads said identifier and communicates to a communication assembly that transmits information of said identifier to an external device, and wherein said external device is configured to transmit an identifier specific protocol to said fluidic device.

* * * * *